US006787125B1

(12) United States Patent
Verwaerde et al.

(10) Patent No.: US 6,787,125 B1
(45) Date of Patent: Sep. 7, 2004

(54) COMPOUND SCREENING METHOD

(75) Inventors: Philippe Verwaerde, Neuville en Ferrain (FR); Christ Platteeuw, Ghent (BE); Gwladys Cuvillier, Gentbrugge (BE); Thierry Bogaert, Kortrijk (BE)

(73) Assignee: Devgen NV, Ghent-Zwignaarde (BE)

( * ) Notice: Subject to any disclaimer, the term of this patent is extended or adjusted under 35 U.S.C. 154(b) by 0 days.

(21) Appl. No.: 09/550,107

(22) Filed: Apr. 14, 2000

Related U.S. Application Data

(60) Provisional application No. 60/129,596, filed on Apr. 15, 1999.

(30) Foreign Application Priority Data

Apr. 15, 1999 (GB) .............................. 9908670

(51) Int. Cl.[7] .............................................. A61K 49/00
(52) U.S. Cl. ........................ 424/9.1; 424/9.2; 424/9.6; 435/4
(58) Field of Search .......................... 424/9.1, 9.2, 9.6, 424/93.1; 435/4; 800/3

(56) References Cited

U.S. PATENT DOCUMENTS

| 4,444,891 A | | 4/1984 | Miwa et al. .................... 436/2 |
| 5,939,021 A | * | 8/1999 | Hansen et al. ................. 422/55 |
| 6,329,566 B1 | * | 12/2001 | Kaplan et al. ................. 800/3 |

FOREIGN PATENT DOCUMENTS

| WO | WO 90/09096 | 8/1990 |
| WO | WO 96/38555 | 12/1996 |
| WO | WO97 11956 A | 4/1997 |
| WO | WO98 51351 A | 11/1998 |
| WO | WO 98/53856 | 12/1998 |
| WO | WO98 54300 A | 12/1998 |
| WO | WO99 02634 A | 1/1999 |
| WO | WO 99/02652 | 1/1999 |
| WO | WO99 05307 A | 2/1999 |
| WO | WO00 34438 A | 6/2000 |

OTHER PUBLICATIONS

N Altan et al., J.Exp.Med., "Defective Acidification in Human Breast Tumor Cells and Implications for Chemotherapy," May 1998, vol. 187, No. 10, pp. 1583–1598.*
N Altan et al., Proc.Natl.Acad.Sci. USA, "Tamoxifen inhibits acidification in cells independent of the estrogen receptor," Apr. 1999, vol. 96, pp. 4432–4437.*
J Stevens et al., Mol Cell Probes, "Quantification of polymerase chain reaction products:enzyme immunoassay based systems for digoxigenin– and biotin– labelled products that quantify either total or specific amplicons," Feb. 1996, 10(1) Abstract.*
EM Denholm et al., Cytometry, "Differential effects of two fluorescent probes on macrophage migration as assessed by manual and automated methods," Apr. 1995, 19(4), Abstract.*

W Obexer et al., Trop Med Parasitol, "A novel in vitro screening assay for trypanocidal activity using the fluorescent dye BCECF–AM," Mar. 1995, 46(1), Abstract.*
KS Mysore et al., Mol Plant Interact, "Role of the Agrobacterium tumefaciens VirD2 protein in T–DNA transfer and integration," Jul. 1998, 11(7), Abstract.*
H Yang et al., Cell Transplant, "In situ assessment of cell viability," Sep.–Oct. 1998, 7(5) Abstract.*
Z Huang et al., J Immunol Methods, "A sensitive competitive ELISA for 2,4–dinitrophenol using 3,6–fluorescein diphosphate as a fluorogenic substrate," May 1992, Abstract.*
A Miyawaki et al., Nature "Fluoresecent indicators for Ca2+ based on green fluorescent proteins and calmodulin," Aug. 1997, vol. 388, pp. 882–887.*
R Kerr et al., West Coast Worm Meeting, "Imaging Calcium in Excitable Cells in *C.elegans*," 1998, Abstract.*
Alexander Kraev et al., "Identification and Functional Expression of the Plasma Membrane Calcium ATPase Gene Family From *Caenorhabditis elegans*," J. Biol. Chem. (1999), vol. 274, No. 7, pgs. 4254–4258.
Arai, Masashi et al., "Alterations in Sarcoplasmic Reticulum Gene Expression in Human Heart Failure," *Circulation Research* (1993) vol. 72, No. 2, pgs. 463–469.
Arai, Masashi, "Function and Regulation of Sarcoplasmic Reticulum $Ca^{2+}$–ATPase," *Jpn. Heart J.* (2000), vol. 41, No. 1, pgs. 1–13.
Del Monte, Federica et al., "Restoration of Contractile Function in Isolated Cardiomyoctes from Failing Human Hearts by Gene Transfer of SERCA1a," *Circulation* (1999), 100:2308–2311.
Kiriazis, Helen et al., "Genetically Engineered Models with Alterations in Cardiac Membrane Calcium–Handling Proteins," *Annu. Rev. Physiol.* (2000), 62:321–51.
MacLennan, David et al., "Minireview: The Mechanism of $Ca^{2+}$–ATPases," *J. Biol. Chem.* (1997), 272:28815–28818.
Miyamoto, Michael et al., "Adenoviral Gene Transfer of SERCA2a Improves Left–Ventricular Function in Aortic–Banded Rats in Transition to Heart Failure," *PNAS* (2000), vol. 97, No. 2, pgs. 793–798.
Moller, Jesper et al., "Structural Organization, Ion Transport, and Energy Transduction of P–Type ATPases," *Biochimica et Biophysica Acta* (1996) 1286, pgs. 1–51.

(List continued on next page.)

*Primary Examiner*—Scott D. Priebe
*Assistant Examiner*—Brian Whiteman
(74) *Attorney, Agent, or Firm*—Wolf, Greenfield & Sacks, P.C.

(57) ABSTRACT

The invention relates to screening methods using nematode worms, particularly but not exclusively *C. elegans*, which are adapted to be performed in a high-throughput format.

27 Claims, 19 Drawing Sheets

OTHER PUBLICATIONS

Odermatt, Alex et al., "Mutations in the Gene–Encoding SERCA1, the Fast–twitch Skeletal Muscle Sarcoplasmic Reticulum $Ca^{2+}$ATPase, are Associated with Brody Disease," *Nature Genetics* (1996) 14(2):191–4.

Sakuntabhai, Anavaj et al., "Mutations in ATP2A2, Encoding a $Ca^{2+}$Pump, Cause Darier Disease," *Nature Genetics* (1999) vol. 21, pgs. 271–277.

Schmidt, U et al.,. "Restoration of Diastolic Function in Senescent Rat Hearts Through Adenoviral Gene Transfer of Sarcoplasmic Reticulum $Ca^{2+}$–ATPase," *Circulation* (2000), 101:790–796.

Rand, J.B. et al. "Genetic Pharmacology: Interaction Between Drugs and Gene Products in *Caenorhabditis Elegans*", *Methods in Cell Biology*, 1995, pp. 187–204, vol. 48(8).

Leitch, G.J. et al. "Use of a Fluorescent Probe to Assess the Activities of Candidate Agents Against Intracellular Forms of Encephalitozoon Microsporidia", *Antimicrobial Agents and Chemotherapy*, 1997, pp. 337–344, vol. 41.

Bernhard, J.M. et al. "Towards a Non–Terminal Viability Assay for Foraminiferan Protists" *Journal of Eukaryotic Microbiology*, 1995, pp. 357–367, vol. 42 (Abstract).

Riddle, D.L. et al. "Responses of the Plant Parasitic Nematodes Rotylenchulus–Reniformis Anguina–Agrostis and Meloidogyne–Javanica to Chemical Attractants", *Parasitology*, 1985, pp. 185–195, vol. 91(1).

Castro, C.E. et al. "Quantitative Bioassay for Chemotaxis With Plant Parasitic Nematodes Attractant and Repellent Fractions for Meloidogyne–Incognita From Cucumber Roots", *Journal of Chemical Ecology*, 1989, pp. 1297–1310, vol. 15(4).

Balan, J. "Measuring Minimal Concentrations of Attractants Detected by the Nematode Panagrellus Redivivus", *J. Chem. Ecol.*, 1985, pp. 105–111, vol. 11(1).

Avery, L. et al. "Effects of Starvation and Neuroactive Drugs on Feeding in *Caenorhabditis Elegans*", *Journal of Experimental Zoology*, 1990, pp. 263–270, vol. 253.

Laughton, D.L. et al. "Reporter Gene Constructs Suggest that the *Caenorhabditis Elegans* Avermectin Receptor Beta––Subunit is Expressed Solely in the Pharynx", *Journal of Experimental Biology*, 1997, pp. 1509–1514, vol. 200.

Brownlee, D.J. et al. "Actions of the Anthelmintic Invermectin on the Pharyngeal Muscle of the Parasitic Nematode, Ascaris Suum", *Parasitology*, Nov. 1997, pp. 553–561, vol. 115(5).

Bennett, J.L. et al. "Micromotility Meter an Instrument Designed to Evaluate the Action of Drugs on Motility of Larval and Adult Nematodes", *Parasitology*, 1986, pp. 341–346, vol. 93(2).

Lorimer, S.D. et al. "A Nematode Larval Motility Inhibition Assay for Screening Plant Extracts and Natural Products", *Journal of Agricultural and Food Chemistry*, 1996, pp. 2824–2845, vol. 44(9).

Hollo, Z. et al. "Calcein Accumulation as a Fluorometric Functional Assay of the Multidrug Transporter", *Biochimica Et Biophysica Acta*, 1994, pp. 384–388, vol. 1191.

Traunspurger, W. et al. "Ecotoxicological Assessment of Aquatic Sediments with *Caenorhabditis Elegans* (Nematoda): A Method for Testing Liquid Medium and Whole–Sediment Samples", *Environmental Toxicology and Chemistry*, 1997, pp. 245–250, vol. 16(2).

Raizen, D.M. et al. "Interacting Genes Required for Pharyngeal Excitation by Motor Neuron MC in *Caenorhabditis Elegans*", *Genetics*, Dec. 1995 pp. 1365–1382, vol. 141.

Sanon, A. et al. "Kinetic Parameters of N–Acetylglucosaminidase in Adult Female *Nippostrongylus Brasiliensis* by a Quantitative Colorimetric Micromethod", *Parasite*, 1996, pp. 115–118, vol. 3(2).

Rogers, W.P. "Enzymes in the Exsheathing Fluid of Nematodes and Their Biological Significance", *International Journal for Parasitology*, 1982, pp. 495–502, vol. 12(6) (Abstract).

Bone, L.W. et al. "Egg Enzymes of the Ruminant Nematode Trichostrongylus–Colubriformis", *International Journal of Invertebrate Reproduction and Development*, 1988, pp. 299–302, vol. 14(2–3).

Thompson, D.P. "Prospects for Rational Approaches to Anthelmintic Discovery", *Parasitology*, 1996 Suppl., pp. S217–S238, vol. 113(Suppl.).

Maule, A.G. et al. "Nematode FMRFamide–Related Peptide (FaRP)–Systems: Occurrence, Distribution and Physiology", *International Journal for Parasitology*, 1996, pp. 927–936, vol. 26(8–9).

Das, A.K. et al. "Simple Micromotility Recorder for Rapid Screening of Potentially Anthelmintic Compounds", *Journal of Pharmacological Methods*, 1988, pp. 323–327, vol. 20(4).

Whitehead, A.G. et al. "Variation in the Development of Stem Nematodes Ditylenchus–Dipsaci in Susceptible and Resistant Crop Plants", *Annals of Applied Biology*, 1987, pp. 373–383, vol. 111(2) (Abstract).

Jenkins, D.C. et al. "The Aggregation Response of Trichostrongylus–Colubriformis A Basis for the Rapid Interpretation of In–Vitro Anthelminitic Screens", *Parasitology*, 1986, pp. 531–537, vol. 93(3).

* cited by examiner

FIG. 4.
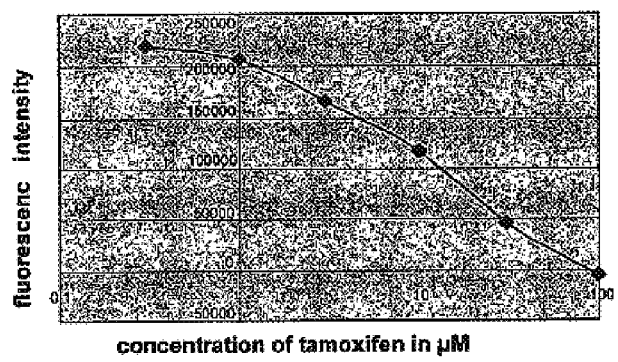
Effect of Tamoxifen
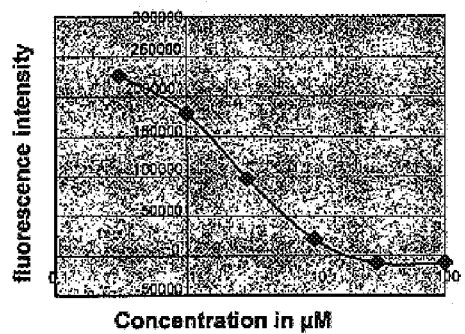
Effect of BP554
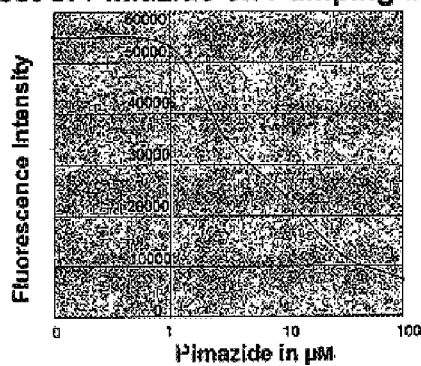
Effect of Pimazide on Pumping in HD8

Effect of Clomipramine effect of thapsigargin on drinking in N2 and HD8 concentration of thapsigargin in μM

FIG. 11. Movement assay OD according to viscosity

FIG. 12. Motility assay according to Uncness

FIG. 13  Motility assay according to Uncness

Egg laying kinetic with N2 in presence of Clomipramine

Egg laying kinetic with N2 in presence of Fluoxetine

Reduction of pharynx pumping by the insecticide Picrotoxinin

Reduction of pharynx pumping by the insecticide Rotenone

Reduction of pharynx pumping by the insecticide dieldrin

Reduction of pharynx pumping by the insecticide ivermectin

COMPOUND SCREENING METHOD

RELATED APPLICATION

This application claims priority under Title 35 §119(e) of U.S. Provisional Application No. 60/129,596, filed Apr. 15, 1999, and entitled COMPOUND SCREENING METHODS and foreign priority benefits under Title 35, U.S.C., §119(a) –(d) or §365(a),(b) of foreign patent application no. GB 9908670.4, filed Apr. 15, 1999, the entire contents of which are incorporated herein by reference.

FIELD OF THE INVENTION

The invention relates to the field of pharmacology and in particular to the screening of chemical substances with potential pharmacological activity using nematode worms such as *Caenorhabditis elegans*. Specifically, the invention relates to methods adapted for high-throughput screening which are performed in a multi-well plate format.

*Caenorhabditis elegans* is a nematode worm which occurs naturally in the soil but can be grown easily in the laboratory on nutrient agar or in liquid nutrient broth inoculated with bacteria, preferably *E. coli*, on which it feeds. Each worm grows from an embryo to an adult worm of about 1 mm long in three days or so. As it is fully transparent at all stages in its life, cell divisions, migrations and differentiation can be seen in live animals. Furthermore, although its anatomy is simple its somatic cells represent most major differentiated tissue types including muscles, neurons, intestine and epidermis. Accordingly, differences in phenotype which represent a departure from that of a wild-type worm are relatively easily observed, either directly by microscopy or by using selective staining procedures.

These characteristics of *C. elegans* make it an extremely useful tool in the drug discovery process. In particular, *C. elegans* may be used in the development of compound screens, useful in the identification of potential candidate drugs, in which worms are exposed to the compound under test and any resultant phenotypic and/or behavioural changes are recorded.

The possibility that *C. elegans* might be useful for establishing interactions between external molecules and specific genes by comparison of *C. elegans* phenotypes which are generated by exposure to particular compounds and by selected mutations is considered by Rand and Johnson in Methods of Cell Biology, Chapter 8, volume 84, *Caenorhabditis elegans*: Modern Biological analysis of an Organism Ed. Epstein and Shakes, Academic Press, 1995 and J. Ahringer in Curr. Op. in Gen. and Dev. 7, 1997, 410–415.

Rand and Johnson in particular describe compound screening assays in which varying concentrations of the compound to be tested are added to nutrient agar or broth which is subsequently seeded with bacteria and then inoculated with worms. Any phenotypic changes in the worm as a result of exposure to the compound are then observed.

Although the nematode, and in particular *C. elegans*, is proving a powerful and efficient tool in the identification or discovery of pharmacologically active molecules, the presently known techniques for compound screening do not readily lend themselves to high throughput screening. This is largely because the known assay techniques rely on visual inspection of worms exposed to the compound under test in order to determine whether the compound has an effect on the phenotype of the worms. Consequently, even if an assay were to be performed in the multi-well assay format necessary for high throughput screening it would be necessary to score each individual well by eye in order to determine the outcome of the assay.

There is thus a need for reliable and reproducible screening methods using live *C. elegans* which do not require scoring by visual inspection and are therefore more suitable for use in automated high throughput screening. The availability of such screening methods would dramatically increase the usefulness of *C. elegans* as a screening tool, enabling researchers to exploit the enormous potential of *C. elegans* as a whole animal system for drug discovery and development.

BRIEF SUMMARY OF THE INVENTION

Accordingly, in a first aspect the invention provides a method of identifying chemical substances which have potential pharmacological activity using nematode worms, which method comprises the steps of:

(a) dispensing substantially equal numbers of nematode worms into each of the wells of a multi-well assay plate;

(b) contacting the nematode worms with a sample of a chemical substance;

(c) detecting a signal indicating phenotypic, physiological, behavioural or biochemical changes in the nematode worms using non-visual detection means.

This method is in effect a standard compound screen in which worms are exposed to candidate compounds and changes in the phenotype, behaviour, biochemistry or physiology of the worms as a result of exposure to the compound are recorded. Such assays may be performed using wild-type nematodes, in which case the 'changes' detected in step (c) will generally be changes away from wild type behaviour etc. However, depending on the type of activity to be detected, compound screens can also be carried out using non wild-type worms, for example mutant or transgenic worms which may display non wild-type characteristics. In this case the 'change' detected in part (c) may be a reversion towards wild-type. Typically, compound screening assays involve running a plurality of assay mixtures in parallel with different concentrations of the chemical substance under test. Typically, one of these concentrations serves as a negative control, i.e. zero concentration of test substance. Changes in behaviour, phenotype, biochemistry or physiology etc resulting from exposure to the compound may then be evaluated in comparison to the negative control.

In a second aspect the invention provides a method of determining the mode of action of a chemical substance using nematode worms, which method comprises the steps of:

(a) dispensing substantially equal numbers of a panel of different mutant nematode worms into each of the wells of a multi-well assay plate;

(b) contacting the nematode worms with the chemical substance; and (c) detecting a signal indicating phenotypic, physiological, behavioural or biochemical changes in the nematode worms using non-visual detection means.

In this method, basic compound screening methodology can be extended to determine the mode of action of a chemical substance. This may be done, for example, by detecting/measuring properties or characteristics of worms exposed to the compound and comparing the result with properties or characteristics of mutant worms carrying mutations in known proteins. Example 4 of the accompanying examples provides an illustration of this in the CNS field.

In a third aspect the invention provides a method of identifying further components of the biochemical pathway on which a compound having a defined effect on nematode worms acts, which method comprises the steps of:

(a) subjecting a population of nematode worms to random mutagenesis;

(b) dispensing one mutagenized F1 nematode worm into each of the wells of a multi-well assay plate;

(c) allowing the F1 nematode worms to generate F2 offspring;

(d) contacting the nematode worms with the compound; and (e) detecting a signal indicating phenotypic, physiological, behavioural or biochemical changes in the nematode worms using non-visual detection means.

This method of the invention is, in effect, a classic a genetic suppressor screen performed in a multi-well format. In a suppressor screen the aim is to identify a mutation which suppresses the phenotype generated by exposure of the worm to a chemical. Worms carrying suppressor mutations are usually identified on the basis that they exhibit a more 'wild type' phenotype in the presence of the compound, as compared to the phenotype generated by exposure of wild type worms to the same compound. Therefore, to identify a suppressor mutant one effectively looks for mutants which exhibit no or minor changes in phenotypic, physiological, biochemical or behavioural characteristics in part (e) following exposure to the compound.

There are many advantages to be gained from performing genetic suppressor screens in a multi-well format, as described by the inventors. In particular, less compound is required to perform an assay in a multi-well plate, as compared to a standard agar plate assay. Furthermore, as the assay in multi-well plates is performed in liquid, compounds to be tested are taken up more efficiently by the nematodes than in a standard plate assay and also compounds tend to precipitate less in liquid than on agar plates, due to the lower concentration.

In a fourth aspect the invention provides a method of identifying chemical substances which modulate the effect of a first compound, which compound has a defined effect on nematode worms, which method comprises the steps of:

(a) dispensing substantially equal numbers of nematode worms into each of the wells of a multi-well assay plate;

(b) contacting the nematode worms with the first compound;

(c) contacting the nematode worms with a further chemical substance; and (d) detecting a signal indicating phenotypic, physiological, behavioural or biochemical changes in the nematode worms using non-visual detection means.

This method may be used to screen for antagonists of a given compound. This principle is illustrated in the accompanying Example 8.

BRIEF DESCRIPTION OF THE FIGURES

FIG. 4 shows dose-response curves for the inhibitors tamoxifen, BP554 and pimazide.

FIG. 18-Picrotoxin, FIG. 19.-Rotenone, FIG. 20.-Dieldrin, FIG. 21-Invention. A reduction in the pharynx pumping rate on exposure to insecticide is clearly seen.

DETAILED DESCRIPTION OF THE INVENTION

Figure 1:
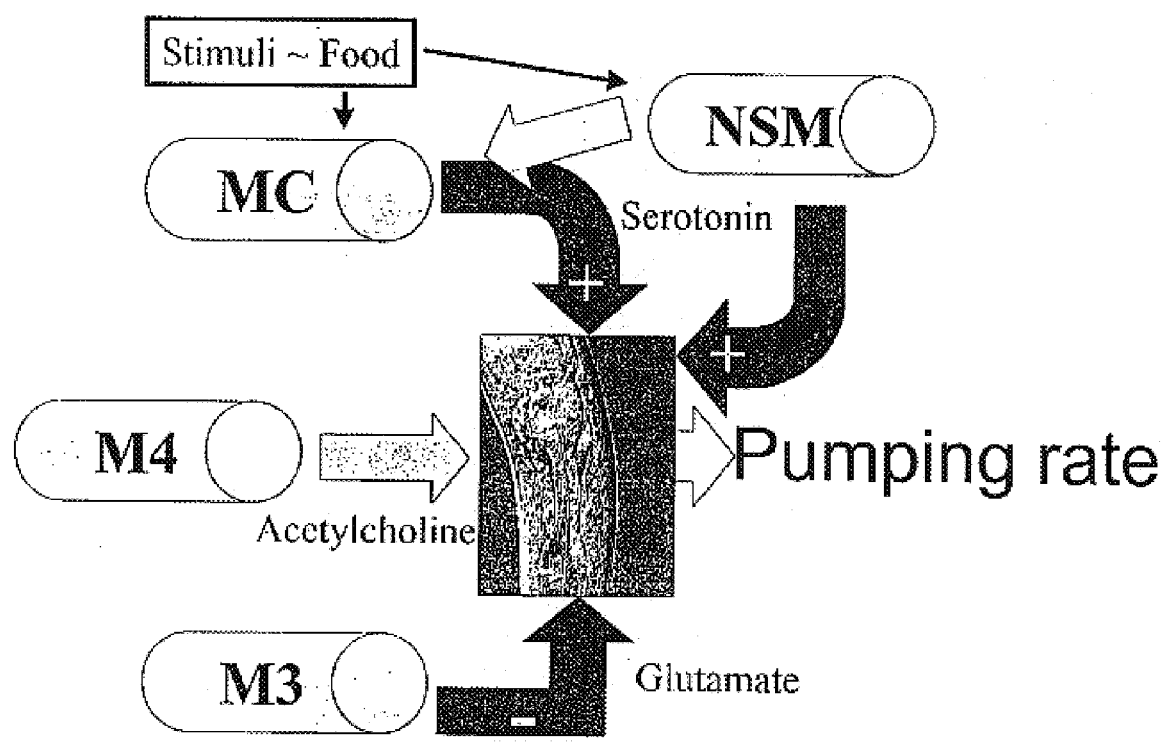
FIG. 1 is an overview of the neurons and transmitters that are known to have a direct influence on the pumping rate of the C. elegans pharynx.

The methods of the invention are all performed in a multi-well plate format and are therefore particularly suitable for use in mid-to-high throughout screening In a preferred embodiment, the multi-well plates have 96 wells, but the invention is also applicable to multi-well plates with another number of wells, which include but is not restricted to plates with 6, 12, 24, 384, 864 or 1536 wells. The terms "multi-well plate" and "microtiter plate" are used interchangeably throught.

As with all the screening methods described herein the above-described methods are preferably performed using nematode worms from the genus Caenorhabditis, most preferably C. elegans or C. briggsae. Although C. elegans and C. briggsaeare preferred, it will be appreciated that the screening methods described herein could be carried out with other nematodes and in particular with other microscopic nematodes, preferably microscopic nematodes belonging to the genus Caenorhabditis. As used herein the term "microscopic" nematode encompasses nematodes of approximately the same size as C. elegans, being of the order 1 mm long in the adult stage. Microscopic nematodes of this approximate size are extremely suited for use in mid- to high-throughput screening as they can easily be grown in the wells of a multi-well plate.

All of the methods of the invention require the detection of a signal which indicates phenotypic, physiological, behavioural or biochemical changes occurring in the nematode worms in the presence of the compound under test. It is an essential feature of the methods of this invention that this signal (also referred to as the read-out) is detected using a non-visual detection means. As used herein the term "non-visual detection means" refers to any means of detecting a signal which does not require visual inspection by the human eye.

The use of a non-visual detection system represents a major advantage over previously known screening methods using which require visual inspection of the nematodes by eye in order to detect gross phenotypic or behavioural changes.

The signal generated as a result of phenotypic, physiological, behavioural or biochemical changes in the nematode worms can be of various types including, for example, a fluorescent, luminescent or colorimetric signal generated in the nematode worms themselves or a change in optical density in a whole suspension of worms.

In one embodiment of the methods a signal is generated by a marker molecule which is added to the worms following contact with the chemical substance under test. The marker molecule is taken up by the worms and the activity of the chemical substance on the nematode worms can then be monitored either directly or indirectly by detecting signal resulting from a change in the properties of the marker molecule as a result of phenotypic, physiological, behavioural or biochemical changes in the worms.

There are various ways in which the worms can take up the marker molecule. For example, worms may take up the marker as a result of the action of a chemical substance under test. Another possibility is that the worms can be pre-loaded with the marker molecule prior to the addition of chemical substance or the marker molecule can be delivered via the media in which the worms are cultured or via bacteria or other food particles on which the worms feed.

Alternatively, the marker molecule can be a genetically encoded marker which is expressed in cells of the nematode worms themselves. Routine methods for the construction of transgenic *C. elegans* are well known in the art and with the use of appropriate promoter sequences transgenic *C. elegans* can be constructed which express a genetically encoded marker molecule in all cells, in a particular tissue or in one or more specified cell types. Suitable genetically encoded marker molecules include autonomous fluorescent proteins (AFPs) such as green fluorescent protein (GFP) and blue fluorescent protein (BFP), aequorin, alkaline phosphatase, luciferase, β-glucuronidase, β-lactamase, β-galactosidase, acetohydroxyacid synthase, chloranphenicol acetyltransferase, horseradish peroxidase, nopaline synthase or octapine synthase.

The marker molecule can also be added to the nematodes as a 'precursor' molecule which can undergo chemical changes in the nematodes as a result of the biochemical activity of the nematode. This biochemical activity on the precursor changes its properties resulting in the generation of a signal which can be measured. A typical example of this system is the use of a precursor marker molecule which can be cleaved by enzymes present in the gut of the nematode worms to generate a marker molecule with a detectable property such as, for example, fluorescence. Examples of such precursor marker molecules include calcein-AM, fluorescein diacetate (FDA) and BCECF-AM which are cleaved by esterases, alkaline phosphatase substrates such as fluorescein diphosphate and AMPPD, aminopeptidase substrates such as CMB-leu, and glucuronidase substrates such as X-gluc.

In order to assist in the measurement of a signal generated using a marker molecule, fluorescence quenchers or luminescence quenchers may be used. For example, a quencher could be added to the medium in order to quench any background fluorescence in the medium, this may make it easier to visualise a fluorescence signal from the gut of the nematodes.

Suitable non-visual detection means include multi-well plate readers, also known as microtiter plate readers or elisa plate readers. The use of microtiter plate readers facilitates high throughput screening to select for active chemical substances with potential pharmacological activity. Suitable multi-well plate readers are commonly used in the art and are available commercially. Such plate readers can be used with a wide range of detection methods including fluorescence detection, luminescent detection, colorimetric detection, spectrophotometric detection, immunochemical detection, radiation detection and optical density detection.

The advantage of multi-well plate readers is that they can be used to make quantitative measurements of the signal generated as a result of the activity of the chemical substances on the nematode worms. The ability to make quantitative measurements means that it is possible to construct quantitative dose response curves of the activity of a chemical compound on the nematodes. Using these dose response curves one can determine the IC50 and ED50 of compounds in nematodes such as *C. elegans*, and hence determine optimal concentrations. Furthermore, the dose response curves enable the determination of any toxic effects of the compound and may also give an indication of possible secondary targets and side-effects of the compound.

Non-visual detection systems other than multi-well plate readers can also be used in the methods of the invention. An example of such a detection system is based on a 'worm dispenser apparatus' which is commercially available from Union Biometrica, Inc, Somerville, Mass., USA. This apparatus has properties analogous to flow cytometers, such as fluorescence activated cell scanning and sorting devices (FACS). Accordingly, it may be commonly referred to as a "FANS" apparatus, for fluorescence activated nematode scanning and sorting device (FANS). The FANS device enables the measurement of properties of microscopic nematodes, such as size, optical density, fluorescence, and luminescence. For screening assays to be performed with a small number of nematodes or for assays that give a faint signal, or for assays for which the presence of food can be a disadvantage in the measurement of the signal, a FANS is a preferred detection instrument. However, the use of a FANS is not limited to these experimental conditions, FANS could be generally used for all the screening methods described herein.

A screening method using a FANS device is quite analogous to the screening method described for the multi-well plate reader. In short, worms are contacted with the chemical substances with or without the addition of a marker molecule. After the appropriate time, the multi-well plates are submitted to the FANS apparatus and in a fully automated procedure the worms are analysed well-by-well for features such as overall size, fluorescence, luminescence or optical density. The desired features are then scored With the use of the FANS device screens can also be performed quantitatively.

In order to generate quantitative results using the methods of the invention it may be important to ensure that substantially equal numbers of individual nematodes are added to each of the wells. The precise number of worms added to the wells may vary depending upon the type of screen being performed and the required sensitivity. In all plate formats, including 96 well plates, it is preferred to use 1 to 100 worms per well, more preferably 10 to 80 worms per well and most preferably 80 worms per well.

Various methods can be used to ensure that substantially equal numbers of worms are added to each of the wells. One way in which this can be achieved is by taking worms cultured according to the standard procedures known to those skilled in the art in solid or liquid media and re-suspending the worms in a viscous solution to form a homogeneous suspension. The viscosity of the solution maintains an even distribution of worms in the suspension, thus substantially equal numbers of worms can be dispensed by adding equal volumes of the homogeneous worm suspension to each of the wells. Suitable viscous solutions include a solution containing a low concentration of a polymer material (e.g. 0.25% low melting point agarose), glycerol etc.

As an alternative to the above-described approach an equal distribution of worms over the wells of the multi-well plate can be achieved using a worm dispensing device, such as that developed by Union Biometrica, Inc. The worm dispenser can be programmed to add a set number of worms to each of the wells of the plate. In addition, it can be used to select worms in such a way that only hermaphrodites or males or dauers are dispensed and it can also select on the basis of size so that specifically eggs, L1, L2, L3, L4 or adult worms are dispensed.

The inventors have observed that use of a viscous medium in the methods of the invention can have advantages over and above ensuring that equal numbers of worms are added to the wells of the multi-well plate. The multi-well screens described by the inventors are performed in liquid medium. However, as the natural environment of nematodes such as *C. elegans* is solid (e.g. soil) growth in liquid medium results in less healthy worms. Worms grown in liquid medium are longer and thinner, the pharynx pumps at a reduced rate, the worms show less movement and lay less eggs. The inventors have found a solution to this problem by adding a water soluble polymer to the medium in order to increase its viscosity (i.e. to produce a viscosity greater than that of normal liquid medium for nematode culture, such as M9). Use of a viscous liquid medium retains the advantages of liquid culture, i.e. ease of handling nematodes in liquid, whilst maintaining the health of the worms. Preferred types of polymer are low melting point agarose, carboxymethyl cellulose and polyethylene glycol (especially PEG8000). The optimum amount of polymer to be added may be determined by routine experiment and may vary depending on the nature of the read-out of the assay. For example, in the 'movement assay' described below addition of 0.3% medium viscosity carboxymethyl cellulose has been determined to be optimal. The inventors have used several viscosity variants of carboxy methyl cellulose cellulose to determine the optimal conditions to perform the screens described herein. In one experiment, three variants of carboxy methyl cellulose, namely low, medium and high viscosity carboxymethyl cellulose provided by Sigma (St. Louis, Mo., USA) were tested at a concentration of 0.3% (see FIG. 11). It was observed that at this concentration the medium and the high viscosity carboxymethyl cellulose showed the best results in the screens. For practical reasons, it is preferred to use medium viscosity carboxymethyl cellulose. A concentration of about 0.3% carboxymethyl cellulose is suitable for the majority of screens. The addition of a water polymer to increase the viscosity of the assay medium may result in a significant improvement in any of the specific types of assays described herein, including the pharynx pumping assays, movement assays, mating assays, egg laying assays and defecation assays, and indeed any other type of assay using nematodes such as *C. elegans* which is performed in a multiwell (microtiter) plate.

The screening assays described herein may also be improved by the addition of a water soluble polymer, possibly at a lower concentration than is required to increase the viscosity of the medium, at a concentration sufficient to prevent the nematodes from sticking to the wells of the microtiter plate.

Due to the nature of the plastic material used for the construction of microtiter plates the surfaces of such plates are generally hydrophobic. Hence, because the outer surface of nematodes such as *C. elegans* is also hydrophobic the nematodes have a preference to stick to the walls of microtiter plates, significantly hampering the performance of assays carried out in microtiter plates. This problem might be avoided with the use of different types of microtiter plates but to date there are no microtiter plates available on the market which sufficiently reduce this problem. The present inventors have now found that the problem of nematodes sticking to the walls of microtiter plates can be overcome by the addition of a suitable concentration of a water soluble polymer to the assay medium.

Preferred types of water soluble polymer are polyethylene glycol (PEG), particularly PEG8000, polyvinyl alcohol (PVA) and polyvinyl pyrrolidone (PVP), with PEG8000 being the most preferred. For a given type of polymer in a given type of screening assay the optimal concentration of polymer to be added to the medium can readily be determined by routine experiment. For PEG8000, a concentration of 0.1% gives good results in most types of screens. Polymer concentrations in the range 0.01% to 10% may also be suitable, depending on the type of assay.

Addition of a polymer to the assay medium results in a particular improvement for assays performed in multi-well plates having more than 96 wells by preventing the worms from sticking to the walls of the wells. Moreover, the presence of the polymer in the medium generally facilitates manipulations of nematodes in liquid culture, such as pipetting and operation of automated dispensing systems such as the FANS device, the Qfit2 device from Genetix (Dorset, UK) and other automated systems used to fill microtiter plates.

The addition of a water soluble polymer to the assay medium in order to prevent the nematodes from sticking to solid surfaces such as the walls of a microtiter plate may result in a significant improvement in any of the specific types of assays described herein, including the pharynx pumping assays, movement assays, mating assays, egg laying assays and defecation assays, and indeed any other type of assay using nematodes such as *C. elegans* which is performed in a microtiter plate.

All of the screening methods described herein can be performed using various kinds of *C. elegans*, including wild-type worms, selected mutants, transgenic worms and humanized worms. The transgenic strains can be strains expressing a transgene in the whole organism, or in a part of the organism, in a single tissue, in a sub-set of cell types, in a single cell type or even in one cell of the organism. The mutant worms may carry a mutation in a single gene or in two or more different genes. Humanized worms are particularly useful for the identification of compounds with potential therapeutic activity in the human pharmaceutical field as they can be used to perform screens which are specifically directed at human target proteins but which have all the advantages of the nematode biology and ease of manipulation.

Standard methods for culturing nematodes are described in Methods in Cell biology Vol. 48, 1995, ed. by Epstein and Shakes, Academic press. Standard methods are known for creating mutant worms with mutations in selected *C. elegans* genes, for example see J. Sutton and J. Hodgkin in "The Nematode *Caenorhabditis elegans*", Ed. by William B. Wood and the Community of *C. elegans* Researchers CSHL, 1988 594–595; Zwaal et al, "Target—Selected Gene Inactivation in *Caenorhabditis elegans* by using a Frozen Transposon Insertion Mutant Bank" 1993, Proc. Natl. Acad. Sci. USA 90 pp 7431–7435; Fire et al, Potent and Specific Genetic Interference by Double-Stranded RNA in *C. elegans* 1998, Nature 391 , 860–811. A population of worms can be subjected to random mutagenesis by using EMS, TMP-UV or radiation (Methods in Cell Biology, Vol 48, ibid). Several selection rounds of PCR could then be performed to select a mutant worm with a deletion in a desired gene. In addition, a range of specific *C. elegans* mutants are available from the *C. elegans* mutant collection at the *C. elegans* Genetic Center, University of Minnesota, St Paul, Minn.

The 'chemical substances' or 'compounds' to be tested in the methods of the invention may be is any foreign molecules not usually present in the worm or to which the worm would not normally be exposed during its life cycle. These terms may be used interchangeably. For example, the worm may be exposed to a chemical substance/compound listed in a pharmacopoeia with known pharmacological activity. Alternatively, the chemical substance/compound may be one known to interact with a particular biochemical pathway or gene. A further alternative is to test known molecules with no known biological activity or completely new molecules or libraries of molecules such as might be generated by combinatorial chemistry. Compounds which are DNA, RNA, PNA, polypeptides or proteins are not excluded.

In one embodiment the methods of the invention are performed using transgenic *C. elegans* expressing a transgene which comprises a 'toxic gene'. In this context the term 'toxic gene' encompasses any nucleic acid sequence which encodes a protein which is toxic to the cell. Suitable examples include nucleic acid encoding ataxin, alpha-synuclein, ubiquitin, the tau gene product, the Huntington's gene product (huntingtin), the best macular dystrophy gene product, the age-related macular dystrophy product or the unc-53 gene product. 'Toxic genes' encoding proteins involved in apoptosis or necrosis could also be used with equivalent effect. Using appropriate tissue-specific or cell type-specific promoters transgenic *C. elegans* can be constructed which express one or more toxic genes in a single tissue, in a subset of cell types, in a single cell type or even in a single cell, for example a single neuron. Expression of the toxic gene will generally result in abnormality/malfunction of the cells and tissues expressing the toxic gene. Many suitable tissue-, cell type- or developmentally-specific promoters are known for use in *C. elegans*.

All of the screening methods described herein can also be performed using synchronized worm cultures. Synchronized worms are worms that are in the same growth stage. The various growth stages of nematode worms such as *C. elegans* are eggs, the L1 stage, L2 stage, L3 stage, L4 stage and adult stage. Furthermore, in a preferred embodiment of the invention, the synchronized nematode worms are of a specific sex.

The synchronized cultures can be hermaphrodites or males or nematodes in special larval stage, designated dauers.

Techniques suitable for use in generating the various synchronized cultures are known in the art, see for example Methods in Cell Biology, vol 48, ibid. The main population of a standard *C. elegans* culture consists of hermaphrodite worms, so it does not require special techniques to generate synchronized hermaphrodite nematodes in different growth stages. To generate male worms, several techniques have been described in the literature. *C. elegans* cultures that are enriched or consist exclusively of male worms, have been described in *C. elegans* 11, ed, By Fiddle, Blumenthal, Meyer and Pries, 1997, CSHL press. Strains for making enriched or pure male samples have been described by Johnathan Hodgkin, Worm breeder's gazette 15(5), 1999). To generate *C. elegans* dauers, several techniques have been described (Elegans 11, ibid). Mainly, a temperature sensitive daf-c mutant of *C. elegans* is used to generate dauers, although other possibilities exist such as daf2-ts mutants which produce 100% dauers at 25° C.

In a particular embodiment of the methods of the invention, the step of detecting a signal indicating phenotypic, physiological, behavioural or biochemical changes in the nematode worms using non-visual detection means comprises detecting changes in the pharynx pumping rate of the nematode worms. These methods may be hereinafter be collectively referred to as 'pharynx pumping assays'.

*C. elegans* feeds by taking in liquid containing its food (e.g. bacteria). It then spits out the liquid, crushes the food particles and internalises them into the gut lumen. This process is performed by the muscles of the pharynx. The process of taking up liquid and subsequently spitting it out is called pharyngeal pumping or pharynx pumping.

Because the process of pharynx pumping involves both the muscles of the pharynx and also pharyngeal neurons, measurement of the rate of pharynx pumping can be exploited to provide a useful screen to identify chemical substances which have an effect on muscle and/or nerve activity.

The rate of pharynx pumping can be readily measured by detecting the accumulation of a marker molecules in the worm gut. If this is done using a multi-well plate reader then the assay can be performed rapidly and quantitatively.

In particular, the pharynx pumping rate may be measured by using a marker molecule precursor which is cleavable by enzymes present in the gut of the nematodes, as described above. Calcein-AM is particularly preferred for this purpose. Calcein-AM is an esterase substrate, and upon cleavage of calcein-AM by esterases, calcein (a fluorescent molecule) is released. As esterases are present in the gut of nematodes such as *C. elegans*, the pharynx pumping rate can be measured indirectly by measuring calcein fluorescence.

In the examples given herein, calcein-AM has been used to measure the rate of pharynx pumping in *C. elegans* in the presence or absence of several chemical substances. These measurements can be performed in a quantitative high throughput way, allowing selection for chemical substances that alter the pumping rate of the *C. elegans* pharynx. This method is not restricted to the use of calcein-AM and other precursor substrates could be used, such as:

With a fluorescent read out:
Esterase substrates. Calcein-AM, FDA, BCECF-AM
Alkaline phosphatase substrates: Fluorescein di phosphate FDP)
Endoprotease; Aminopeptidase substrates: CMB-leu With a luminescent read out:
Alkaline phosphatase substrates: AMPPD With a colour read out:
Glucuronidase substrates: X-gluc This list is not exclusive, marker molecule precursors can also be found or developed which are cleavable by other enzymes present in the *C. elegans* gut, such as DNAses, ATPases, lipases, amylases, etc. Once such a marker precursor enters the gut, it is cleaved to release the detectable marker which can then be monitored. Thus, it is possible to measure the rate of pharynx pumping indirectly by measuring the accumulation of a detectable marker molecule in the gut.

The pH of the *C. elegans* gut is low, therefore molecules that becomes fluorescent at a low pH are useful tool to assess the rate of pharynx pumping. LysoSensor green from Molecular probes exhibits such properties and has been successfully used to assess pharynx pumping. The fluorescence observed in the gut is similar, but less bright, to the fluorescence obtained with calcein-AM. However, marker molecules which are fluorescent at low pH have the additional advantage that they can be used together with a nematode food source, e.g. bacteria, which then should not interfere with the read-out as it is dependent only on a pH change and is not enzyme related.

LysoSensor marker molecules or probes are weak bases that are selectively concentrated in acidic organelles as a result of protonation. This protonation also relieves the fluorescence quenching of the dye by its weak-base side chain. Thus, the LysoSensor dyes become more fluorescent in acidic environments. The blue-fluorescent LysoSensor Blue and green-fluorescent LysoSensor Green probes are available with optimal pH sensitivity in either the acidic or neutral range (pKa ~5.2 or ~7.5). With their low pKa values, LysoSensor Blue DND-167 and LysoSensor Green DND are almost nonfluorescent except when inside acidic compartments.

The pharynx pumping assays can also be performed using mutant *C. elegans* strains which have a constitutively pumping pharynx or by using transgenic strains which also exhibit this phenotype. By using a wild-type strain or the constitutive pharynx pumping strain, it is possible to identify chemical substances that enhance, inhibit or modulate pumping rate, respectively.

As the pharynx of the nematode *C. elegans* is a muscle and the pumping rate is mainly governed by some selected neurons, measuring changes in the pharynx pumping rate is a good tool to study neurotransmitter signals and the stimulation of muscles. As the rate of pharynx pumping can be measured quantitatively and a method has been developed to screen for chemical substances which influence this pumping rate, the present invention is a method to screen and isolate chemical substances with potential pharmacological activity.

Chemical substances that influence the pharynx pumping rate will most probably be substances that have an activity on general muscle biology, and/or on neurotransmitter pathways. Examples of proteins which can be the target of these chemical substances are neurotransmitter receptors such as muscarinic receptors, glutamate receptors, hormone receptors and 5-HT receptors, cannabinoid receptors, adrenergic receptors, dopaminergic receptors, opioid receptors, GABA receptors, adenosine receptors, VIP receptors and nicotinic receptors, proteins involved in neurotransmitter synthesis, neurotransmitter release pathway proteins, G-protein coupled receptor proteins. Furthermore proteins for G-protein coupled second messenger pathways such as adenylate cyclase, protein kinase A, cAMP responsive element binding proteins, IP3, diacylglycerol, protein kinase C phospholipase A-D, phosphodiesterases, and proteins encoding for functions in gap junctions, proteins involved in oxidative phosphorylation in mitochondria and proteins involved in other energy-related pathways, ion channel proteins and ion pump proteins are also potential targets for such chemical substances. Examples of such ion channels are sodium/calcium channels, calcium channels, sodium channels and chloride channels. In general, drugs or chemical substances that affect the pumping rate of the *C. elegans* pharynx and which are identified using the pharynx pumping screen will most probably be compounds that show the following activities:

molecules that have influence on neurotransmitter molecules or that are precursors for the synthesis of a neurotransmitter, molecules that enhance, inhibit or modulate the synthesis of a neurotransmitter, molecules that have a function in the depletion of the transmitter, molecules that prevent or stimulate the release of the transmitter from the synaptic vesicles in the synaptic cleft, molecules that function as a receptor inhibitor or stimulator, molecules that mimic the transmitter molecules that function as conduction inhibitors or activators, molecules that function as an activator or inhibitor of the conduction blockade, molecules that prevent or stimulate the re-uptake of transmitter after firing of the neuron, molecules that function as a false transmitter (+/−), molecules that prevent or stimulate receptor clustering, molecules that act in novel pathways.

Thus, the pharynx pumping assays can be used to screen for a broad range of chemical substances with potential pharmacological activity that may have a therapeutic use as anti-psychotic, anti-depressant, anxiolytic, tranquillizer, anti-epileptic, muscle relaxant, sedative or hypnotic agents. The assays may also be used to identify chemical substances that may effect Parkinson's disease and Alzheimer's disease. Furthermore, anti-pruritic, anti-histaminic, and anti-convulsant drugs may also be isolated using the pharynx pumping assay. The pumping assay may also be used to identify nematocides and insecticides.

The pharynx pumping assay may also be used to identify chemical substances which modulate the neurotransmitter pathways involving acetylcholine, dopamine, serotonin, glutamate, GABA and octopamine. This can be achieved by using selected mutant *C. elegans* which exhibit altered levels of one or more of the above-listed neurotransmitters.

With the pharynx pumping assay there is the potential to screen for 10 to 15 modes of action and for 2 to 6 neurotransmitter pathways and ion channels. As both activation as inhibition can be observed, this screening method will make it possible to screen for 40 to 180 targets in a single screen.

The pharynx pumping assay methodology can, in addition to the screens described above, be adapted for use in determining the mode of action of a chemical substance, or to select for chemical substances which act on a specific target In order to perform a screen to identify the mode of action of a compound substantially equal numbers of a panel of different defined mutant, transgenic or humanized nematodes are dispensed into the wells of a multi-well assay plate. A sample of the chemical substance under test is then added to each of the wells and changes in the rate of pharynx pumping are detected as described above. For each of the mutant, transgenic or humanized strains the rate of pharynx pumping in the absence of any chemical substances is also scored. The pharynx pumping assay can thus be used to identify chemicals which enhance or suppress the rate of pharynx pumping in a defined mutant, transgenic or humanized strain.

The examples given herein list several mutant and transgenic *C. elegans* strains which are useful in this aspect of the invention. Mainly these mutants and transgenics relate to neurotransmitter synthesis, neurotransmitter signal transduction and ion channels. More specifically, examples of mutant, transgenic and humanized worms are given which relate to neurotransmitter receptors such as muscarinic receptors, glutamate receptors, hormone receptors, 5-HT receptors, cannabinoid receptors, adrenergic receptors, dopaminergic receptors, opioid receptors, GABA receptors, adenosine receptors, VIP receptors and nicotinic receptors, proteins involved in neurotransmitter synthesis, neurotransmitter release pathways and G-protein coupled receptor proteins, G-protein coupled second messenger pathways such as adenylate cyclase, protein kinase A, cAMP responsive element binding proteins, IP3, diacylglycerol, protein kinase C, phospholipase Q and proteins encoding for functions in gap junctions, ion channel proteins and ion pump proteins. A non-exhaustive list of well known mutants which are suitable for use in this aspect of the invention is provided in the examples given herein.

Using such mutant, transgenic or humanized strains it is possible to screen for chemical substances which act on a specified target and thus identify a broad range of chemical substances that may have a therapeutic use as anti-psychotics, anti-depressants, anxiolytics, tranquillizers, anti-epileptics, muscle relaxants, sedatives or hypnotics, but the screen will also result in chemical substances that may have an effect on Parkinson's disease and Alzheimer's disease. Furthermore, anti-pruritic, anti-histaminic, and anti-convulsant drugs may be isolated. The transmitter pathway that maybe effected by chemical substances and hence may be detected by the assay are the pathways for acetylcholine, dopamine, serotonin, glutamate, GABA and octopamine. Using appropriate transgenic, mutant or modified strains, it is possible to screen for chemicals which act in specific targets and thus identify also insecticides and nematocides.

These mutant, transgenic and humanized worms also allow the development of screens for chemical substances that have an activity in well-defined biochemical pathways. For example, it is possible to screen for compounds that rescue the phenotype of selected mutant *C. elegans* which carry a defined mutation in a known gene or compounds which enhance the phenotype of the selected mutant *C. elegans*.

In a particularly important embodiment of the invention, the pharynx pumping screen may used to screen for compounds having potential insecticidal activity. The inventors have observed that exposure of *C. elegans* to compounds having pesticidal activity, such as herbicides, insecticides, nematocides or fungicides, has an effect on the pharynx pumping rate. This is illustrated in the accompanying FIGS. 18 to 21 which show the effects of known insecticides on the pharynx pumping rate of *C. elegans*, as measured using the pharynx assay methodology. Hence, the pharynx pumping screen can readily be adapted to screen for compounds having pesticidal activity.

In another embodiment of the invention the pharynx pumping assay methodology can be used to identify further components of the biochemical pathway on which a compound having a defined effect on nematode worms acts. Using this screen it is possible to identify genes that enhance, suppress or modulate the activity of a selected compound. The screen can be done directly and rapidly as using multi-well plates thousands of worms can be screened at once.

First, a random pool of mutant worms is generated. Several techniques such as EMS mutagenesis, TMP-UV mutagenesis and radiation mutagenesis have been described to generate mutant worms (Methods in Cell biology, Vol. 48, ibid). One mutagenized F1 nematode is then dispensed into each of the wells of the multi-well plate and the F2 generation are allowed to produce offspring in the wells. A sample of a compound that has a known activity on the nematode worms is then added to the F2 worms. Changes in the pharynx pumping rate are then monitored as described above, for example using a marker molecule or a marker molecule precursor.

Mutant worms are scored in which the effect of the compound on the pharynx pumping rate is suppressed, enhanced or modulated. These mutant worms will have mutations in one or more genes that are affected by the compound. The mutated gene or genes can then be isolated using standard genetic and molecular biology techniques. These genes, and their corresponding proteins, are considered to be important genes and proteins of the affected pathway, and hence are putative new targets for the further development of screens in the drug discovery process. As with all the methods described herein, this method is preferably performed using microscopic nematodes, particularly worms of the genus Caenorhabditis and most preferably *C. elegans*.

In still another embodiment of the invention the pharynx pumping assay methodology can also be used to screen for chemical substances that are enhancers, suppressors or modulators of a selected chemical compound having a defined effect on nematode worms.

In this assay worms are placed in multi-well plates with a compound that has known effect on the pharynx pumping rate of nematode worms. A second chemical substance is then added to each of the wells and chemical substances which enhance, reduce or modulate the effect of the selected compound are identified by detecting changes in the pharynx pumping rate of the nematode worms using the methods described above. This method is useful to screen for chemical substances that are active in a selected biochemical pathway. The chemical substances thus isolated can be putative therapeutics, or can be considered as hits for further drug development.

In a still further embodiment of the pharynx pumping assay, the assay is performed using *C. elegans* which are transgenic, or mutant or humanized for the Sarco/endoplasmic reticulum calcium ATPase gene (SERCA) and/or for its regulators Phospholamban (PLB) and Sarcolipin (SLN). These genes are important for the regulation of the internal storage of calcium in the cell.

Chemical substances that alter the pumping rate of the pharynx in these mutant, trarsgenic or humanized worms are substances that modulate the activity of SERCA or PLB or SLN or that alter the interaction of SERCA-PLB or that alter the interaction of SERCA-SLN or that alter the activity of the SERCA pathway. Such chemical substances may be useful as therapeutics or may be hit compounds useful for further drug development in the area of cardiovascular diseases including hypertension, cardiac hypertrophy and cardiac failure, but also in the area of diabetes mellitus and in the area of skeletal muscle diseases including Brody disease.

In a still further embodiment of the pharynx pumping assay the assay may be performed using nematodes which exhibit aberrant pharynx morphology and/or function.

The pharynx of the nematode consists of several cell types and all of these are required for the pharynx to function properly. In addition, pharynx pumping is regulated by several neurons. The cells essential for pharyngeal morphology and pharyngeal function are the pharyngeal muscles, the pharyngeal epithelial cells, the pharyngeal glands and the pharyngeal neurons. If one of these cell types is altered, degenerated or dysfunctional, the pharynx will have an aberrant morphology or an aberrant function which results in an altered pumping of the pharynx.

The examples given below list known *C. elegans* mutants that exhibit an altered pumping rate as a result of an altered pharyngeal morphology. In addition, it is possible to generate *C. elegans* worms which exhibit a defect in one or more of the cell types required to maintain the morphology and/or function of the *C. elegans* pharynx. This can be achieved by expressing 'toxic genes' in cells of the pharynx. In this context the term 'toxic genes' encompasses any nucleic acid sequence which encodes a protein which is toxic to the cell. Suitable examples include nucleic acid encoding ataxin, alpha-synuclein, ubiquitin, the tau gene product, the Huntington's gene product (huntingtin), the best macular dystrophy gene product, the age-related macular dystrophy product or the unc-53 gene product. 'Toxic genes' encoding proteins involved in apoptosis or necrosis could also be used with equivalent effect. Expression of the toxic genes in the pharynx or in particular cell types within the pharynx can be achieved using tissue-specific or cell type-specific promoters which are capable of directing the appropriate expression pattern. For example, the myo-2 promoter can be used to direct expression in the pharynx and the unc-129 promoter can be used to direct expression in the pharyngeal neurons. Other suitable promoters included the tropomyosin promoter tmy-1 and the daf-7 promoter. Expression of a toxic gene in one or more cell types of the pharynx or in the pharyngeal neurons will result in a changed morphology and/or function of the pharynx, and hence an alteration of the pharynx pumping rate. Interestingly, disruption of the ASI neuron by expression of a toxic gene under the control of the daf-7 promoter results in dauer formation. This is directly the result of a lack of insulin hence *C. elegans* in which the ASI neuron is disrupted can be used to perform screens which may be useful in relation to diabetes. These screens could be performed using the pharynx pumping assay read-out or alternatively the movement assay read-out described below (see example 12). Mutant or transgenic worms which exhibit an altered pharynx pumping rate can be used to screen for chemical substances which further alter the pharynx pumping rate e.g. which rescue the mutant/ transgenic phenotype or which enhance the mutant/ transgenic phenotype. The chemical substances thus isolated may be useful as therapeutic agents or as hit compounds for further drug development in disease areas such as anti-depressants, anti-psychotics, anxiolytics, tranquillizers, anti-epileptics, muscle relaxants, sedatives, anti-migraine drugs, analgesics and hypnotics. Furthermore, by altering the nature of the toxic gene expressed in cells of the pharynx/ pharyngeal neurons chemical substances will be isolated that are useful in the development of treatments for Parkinson's disease, Alzheimer's disease, Lewy body disease, Best macular dystrophy, age-related macular dystrophy and polyglutamine-induced diseases such as Huntington's disease, Kennedy's disease and ataxia. Mutant or transgenic worms which exhibit an altered pharynx pumping rate may further be used to screen for pesticides such as herbicides, nematocides, insecticides and fungicides.

The performance of the pharynx pumping assays described herein may be improved by adding a water soluble polymer to the assay medium in order to increase the viscosity of the assay medium. Preferred types of polymer are carboxymethyl cellulose, polyethylene glycol (especially PEG8000) and low melting point agarose. For any given type of polymer and type of pharynx pumping assay, the optimum concentration of polymer added to the medium may be determined by routine experiment. As illustrated in the accompanying FIGS. 14 and 15, addition of a polymer to increase the viscosity of the assay medium results in increased pharynx pumping in *C. elegans*. It is thought that the use of a more viscous medium may mimic the more solid conditions in which *C. elegans* naturally lives.

The performance of the pharynx screens may also be improved by the addition of a water soluble polymer to the assay medium at a concentration sufficient to prevent the nematode worms from sticking to the wells of the multi-well plate. Preferred types of polymer are polyethylene glycol, particularly PEG8000, PVA and PVP, with PEG8000 being most preferred. For any given type of polymer and type of pharynx pumping assay, the optimum concentration of polymer added to the medium may be determined by routine experiment. For PEG8000, a concentration of 0.1% is particularly preferred.

The inventors have observed that addition of PEG to the assay medium in the pharynx pumping assay results in an increased quality, mainly due to a reduction in the numbers of dead or harmed individuals. During the setting up of the assay the nematodes need to be divided over the different wells and plates, either manually or using automated systems. During these manipulations of the nematodes, there is a risk that the worm will stick to the wall of the pipette or other tool. The flow of the medium in which the nematode is suspended may then result in the death of the worm. One may conclude that addition of PEG8000 to the medium, results in more pumping and less variation in the pharynx pumping assay (see FIG. 10).

In a further embodiment of the invention the step of detecting a signal indicating a phenotypic, physiological, behavioural or biochemical changes in the nematode worms using non-visual detection means comprises detecting changes in the intracellular levels of ions, metabolites or secondary messengers in cells of the nematode worms. In this particular embodiment of the invention, the activity of a chemical substance is not detected indirectly be measuring a signal from a marker molecule, but by measuring the activity of genetically encoded sensor whose properties are altered in the presence of specific ions, metabolites or secondary messengers. For example, changes in intracellular levels of $Ca^{2+}$ can be detected using the genetically encoded calcium sensor molecules GFP-calmodulin or aequorin.

GFP-calmodulin is known to be fluorescent in the presence of calcium ions. Thus, when intracellular calcium levels are low, no fluorescence can be detected but if the calcium levels increase calcium binds to the GFP-almodulin causing a confirmation change which results in a fluorescent molecule which can be detected, for example using a multi-well plate reader. Other genetically encoded sensor molecules could be used whose fluorescent or luminescent properties are altered in the presence of secondary messengers such as, for example, cAMP, diacylglycerol or inositol triphosphates (IP3).

Preferably this aspect of the invention is carried out using transgenic C. elegans which express the genetically encoded sensor in all cells, or in specific tissues, or in selected cells. This can be achieved with the use of tissue-specific or cell type-specific promoters with suitable activity. The method cen be performed using transgenic worms which express GFP-calmodulin in any cells/tissues of the nematode which are sensitive to calcium signalling, including cells of the pharynx, the vulva muscles, the body wall muscles and neurons. As in previous examples, the transgenic worm can be of wild-type genetic background, a mutant transgenic or a humanized strain. As intracellular calcium levels in the cells of the pharynx are correlated with the pharynx pumping rate, the fluorescence detected in transgenic nematodes expressing GFP-calmodulin in these cells is an indication of the pharynx pumping rate and these transgenic worms can also be used to screen for chemical substances that influence the pumping rate of the pharynx. In a still further embodiment of the invention, the step of detecting a signal indicating a phenotypic, physiological, behavioural or biochemical changes in the nematode worms using non-visual detection means comprises detecting changes in the movement behaviour of the nematode worms.

Nematode worms that are placed in liquid culture will move in such a way that they maintain a more or less even (or homogeneous) distribution throughout the culture. Nematode worms that are defective in movement will precipitate to the bottom in liquid culture. Due to this characteristic of nematode worms as result of their movement phenotype, it is possible to monitor and detect the difference between nematode worms that move and nematodes that do not move.

The movement of nematode worms is mainly the result of the action of the body wall muscles and is regulated by neuronal activity. Accordingly, screens based on detection of altered movement behaviour can be developed to identify chemical substances which may have an effect on muscle and/or neuronal activity.

Advanced multi-well plate readers are able to detect sub-regions of the wells of multi-well plates. By using these plate readers it is possible to take measurements in selected areas of the surface of the wells of the multi-well plates. If the area of measurement is centralized, so that only the middle of the well is measured, a difference in nematode autofluorescence (fluorescence which occurs in the absence of any external marker molecule) or optical density can be observed in the wells containing nematodes that move normally as compared to wells containing nematodes that are defective for movement. For the wells containing the nematodes that move normally, a low level of autofluorescence or optical density will be observed, whilst a high level of autofluorescence or optical density can be observed in the wells that contain the nematodes that are defective in movement. Optical density is measured using a variation of the platelet aggregation assay, which is well known in the art. Using the MRX revelation device from Dynex (USA), optical density can be measured at multiple points per well, showing the precipitation pattern of the nematodes.

In an adaptation of the movement assay, autofluorescence or optical density measurements can be taken in two areas of the surface of the well, one measurement in the centre of the well, and on measurement on the edge of the well. Comparing the two measurements gives analogous results as in the case if only the centre of the well is measured but the additional measurement of the edge of the well results in an extra control and somewhat more distinct results.

The movement assay can be used for the same purposes as the pharynx pumping assay described above i.e. the movement assay can be used to identify chemical substances that alter the movement behaviour of the nematode and hence may have an effect on muscle and/or neuronal activity, for the identification of genetic enhancers, suppressors and modulators of a selected compound having a known effect on nematode worms or for the identification of chemical substances that are enhancers, suppressors or modulators of a selected compound. Chemical substances which are identified using the movement assay as having an effect on the movement behaviour of nematode worms (summarised in Table 10) are generally found to belong to the class of CNS-related drugs but also include GABA antagonists, NMDA antagonists, m-Glu antagonists and adrenergic antagonists.

The movement assay is based on the principle that moving nematodes will stay suspended in the medium, whilst nematodes which do not move anymore will sink to the bottom of the well. This difference in the location of the nematodes results in a difference in OD when measured centrally in the well as previously described. Although moving worms stay diluted in the medium they tend to sink down over time as a result of gravity pull.

The inventors have observed that this problem may be overcome with the addition of a polymer to the liquid medium in order to increase the viscosity of the medium. The increased viscosity allows for more resistance to the moving worm and hence better suspension in the medium. The inventors have tested low, medium and high viscosity variants of carboxymethyl cellulose (from Sigma, St. Louis, Mo., USA and described hereinbefore) to determine optimal conditions for the movement assay. A concentration of 0.3% medium viscosity carboxymethyl cellulose was determined to be optimal. This effect is not, however, limited to carboxymethyl cellulose and similar improvement in the movement assay can be achieved using other types of water soluble polymer, for example low melting point agarose, PEG etc. The precise concentration of polymer used in any given assay is, of course, dependent on the specific type of assay one wishes to perform; if the polymer concentration is too low the viscosity of the medium will be insufficient, too high a concentration of polymer will result in formation of a gel, preventing non-moving worms from sinking during the assay. For any given type of polymer and type of assay, the concentration of polymer required for optimum performance of the assay can readily be determined by routine experiment.

Figure 12:
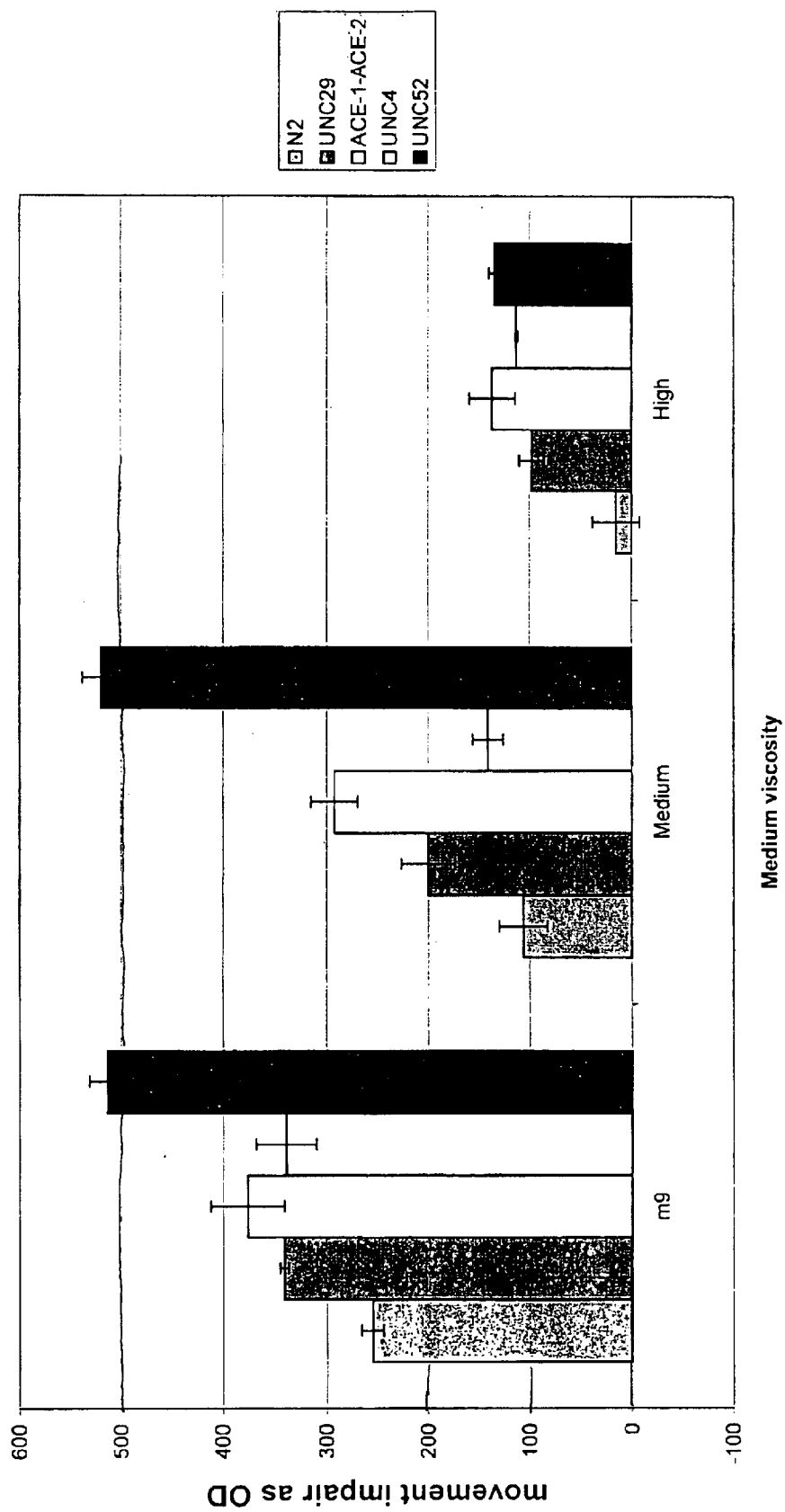
FIG. 12 and FIG. 13 illustrate the effect of viscosity of the medium on performance of the movement assay for various C. elegans mutants in a comparative study. 100 worms were incubated in a round bottom shaped microtiter plate. OD was measured at 340 nm in various viscous media (M9, medium viscosity carboxymethylcellulose and high viscosity carboxymethylcellulose). Measurements were done in triplicate.
Figure 13:
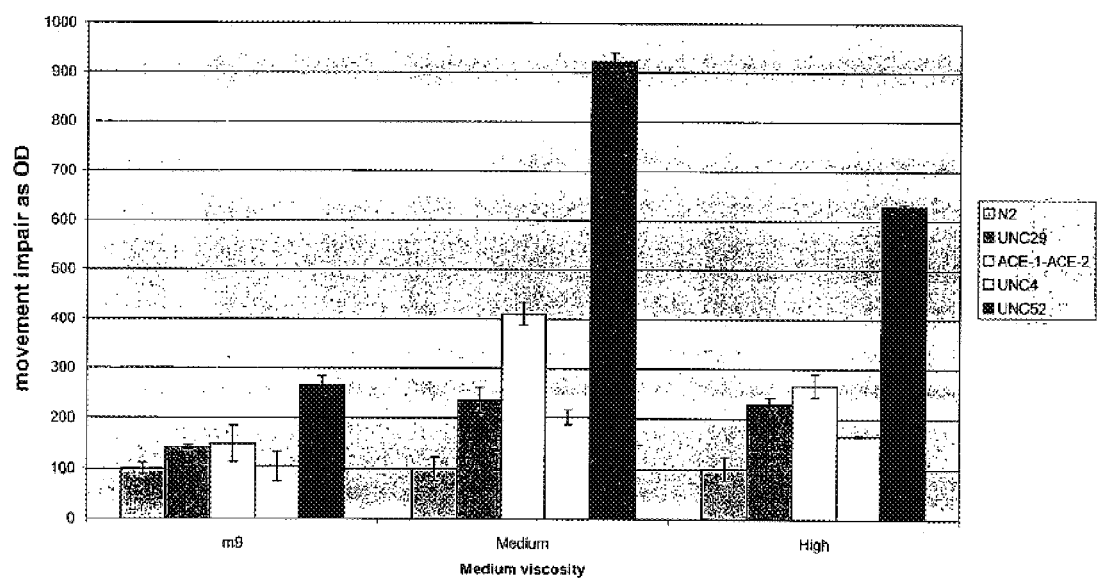

The effect of viscosity in the movement assay has been determined for various C. elegans mutants in a comparative study, the results of which are illustrated in FIGS. 12 and 13. In this study C. elegans Unc and Ace mutants having movement defects were compared with each other and with wild-type C. elegans N2, in M9 medium and media with varying viscosity. The results of this experiment illustrate that medium to high concentrations of carboxymethyl cellulose improve the movement assay.

The performance of the movement assays described herein may further be improved by the addition of a water soluble polymer to the assay medium at a concentration sufficient to prevent the nematode worms from sticking to the wells of the multi-well plate. Preferred types of polymer are polyethylene glycol, particularly PEG8000, PVA and PVP, with PEG8000 being most preferred. For any given type of polymer and type of movement assay, the optimum concentration of polymer added to the medium may be determined by routine experiment. For PEG8000, a concentration of 0.1% is particularly preferred.

As with the other screening methods described herein the movement assay methods are preferably carried out using microscopic nematode worms, particularly those of the genus Caenorhabditis and most preferably C. elegans. The movement assay can be performed using synchronised worm cultures at different growth stages, using male, hermaphrodite or dauer worms or using mutant, transgenic or humanized worms. One mutant C. elegans strain, the ace-1; ace-2 double mutant, is particularly suitable for use in movement assays. This strain does not show any movement and has a spasm-like phenotype. It can therefore be used to screen for chemical substances which rescue the defective movement phenotype. These chemical substances may have a pharmacological effect on muscle and/or neuronal activity.

In a still further embodiment of the invention the step of detecting a signal indicating a phenotypic, physiological, behavioural or biochemical changes in the nematode worms using non-visual detection means comprises detecting changes in the mating behaviour of nematode worms.

The mating behaviour of nematodes such as C. elegans is very complex, involving at least following steps: recognition, backing, tail curling, vulva location and copulation. To perform this behaviour, the male nematode has at least 41 specialized additional muscles, 79 additional neurons, 36 extra neuronal support cells, 23 proctodeal cells, and 16hypodermal cells associated with mating structures. The function of some of the neurons has been described. Also several mutants have been described that show defects in mating behaviour (C. elegans II, ibid; J. Sulton et al., W13G 7(2)22; Loer and Kenyon WBG 12(2).80, 1992; Hadju et al., International worm meeting abstract 151, 1991). Due to the complex nature of the mating behaviour, several conditions and mutants have been described to enhance mating behaviour in C. elegans. One of these is the use of hermaphrodites with a decreased movement, such as the unc-52 (e444) mutant which shows paralysed behaviour at adulthood.

Because mating involves the activity of both muscles and neurons, screens based on detecting changes in the mating behaviour of nematode worms(the mating assay) can be used to identify chemical substances which may modulate muscle and/or neuronal activity. The mating assay can be used to isolate chemical substances that modulate mating, or to isolate chemical substances that modulate the activity of a compound that effects mating behaviour, or to isolate genes and pathways that are active in the mating behaviour, or to isolate genes and pathways that modulate the activity of a compound that affects mating behaviour. In other words, the mating assay can be used for all the same purposes as the pharynx pumping assays and movement assays described above.

C. elegans are not able to perform mating in liquid media The high-throughput screens based on mating behaviour are therefore performed in semi-liquid conditions. A low-melting agarose solution of approximately 0.5% is suitable for this purpose. This semi-liquid medium gives sufficient support for the nematodes to move toward each other and to perform mating. Addition of other polymers to obtain suitably viscous medium may also be used in the mating assay.

Mating performance is measured by measuring the number of eggs or offspring produced from a mating experiment. In a particular embodiment of the invention specific strains are used which are not able to generate offspring by self-fertilization. Such so-called hermaphrodite 'non-selfers' cannot generate offspring, but hermaphrodites that have mated will generate offspring. The offspring can be measured directly by the previous described movement test, or a marker dye can be added to the medium such as calcein-AM so that the previously described pharynx pumping screen can be performed. Alternatively, specific antibodies and fluorescent antibodies can be used to detect the offspring. Any specific antibody that only recognizes eggs, or L1 or L2 or L3 or L4 stage worms, will only recognize offspring, by way of example an antibody that recognizes an antigen on the surface of C. elegans L1 larvae has been described by Hemmer et al., (1991) J Cell Biol, 115(5): 1237–47. Finally, the number of eggs or offspring in each well can be counted directly using a FANS device.

In another embodiment of the invention either the male worms or the hermaphrodite worms can be transgenic worms which stably express a marker molecule such as an autonomous fluorescent protein (GFP or BFP) or a luminescent marker in some or all cell types. The offspring generated from mating of these transgenic worms will also express the marker molecule and hence can be easily measured using a multi-well plate reader or a FANS device. In the case that the male worms are the transgenic worms expressing the marker then the hermaphrodites do not need to be 'non-selfers' since only offspring resulting from the mating of males and hermaphrodites will express the marker whilst offspring generated from hermaphrodite self-fertilization will not harbor the marker molecule. The offspring resulting from mating and self-fertilization can thus be distinguished. In the case that the hermaphrodite worm is the transgenic strain expressing the marker molecule the hermaphrodite strain is preferably also a 'non-selfer' strain.

The mating assay can also be performed using C. elegans in which the function of a male-specific neuron involved in mating behaviour is disrupted. The examples included herein provide a list of male-specific neurons involved in mating behaviour. The function of one or more of these neurons can be disrupted for example by expression of one of the toxic genes listed above in connection with the pharynx pumping assays. By using C. elegans which have defects in one or more specific neurons it is possible to perform screens to identify chemical substances which act on a specific neuronal signalling pathway. The chemical substances identified using such screens may have CNS-related pharmacological activity.

The mating assay can also be performed using transgenic C. elegans which exhibit altered mating behaviour as a result of the expression of a toxic gene in a specific tissue or cell type. Suitable transgenic C. elegans can be constructed according standard techniques known in the art using one of the toxic genes listed above under the control of an appropriate tissue- or cell type-specific promoter. Promoters which may be useful for this purpose include the her-i P2 promoter which directs gene expression in CP9, the mab-18 (alternative splice of pax-6 homologue vab-3) promoter which directs gene expression in ray 6 and the spe-TI promoter which directs gene expression in 60 cells of the spermatheca. In a still further embodiment of the invention the step of detecting a signal indicating a phenotypic, physiological, behavioural or biochemical changes in the nematode worms using non-visual detection means comprises detecting changes in the egg laying behaviour of the nematode worms.

The vulva of hermaphrodite C. elegans nematodes contains at least 24 cells and several neurons, of which the HSN neurons are considered to be the most important in egg-laying. Furthermore at least 8 uterine muscles have been described. Several mutants have been described in gonad development, egg-laying, vulva development and function (The nematode Caenorhabditis elegans, ibid.; C. elegans II, ibid.), Accordingly, high-throughput screening assays can be developed which use a read-out based on detection of changes in the egg laying behaviour of nematodes such as C. elegans. Again, assays based on detection of egg laying can be used for the same purposes as the pharynx pumping and movement assays described herein. In these assays the number of eggs layed is detected by counting the numbers of resultant offspring using the techniques described above for the mating assay.

Figure 6:
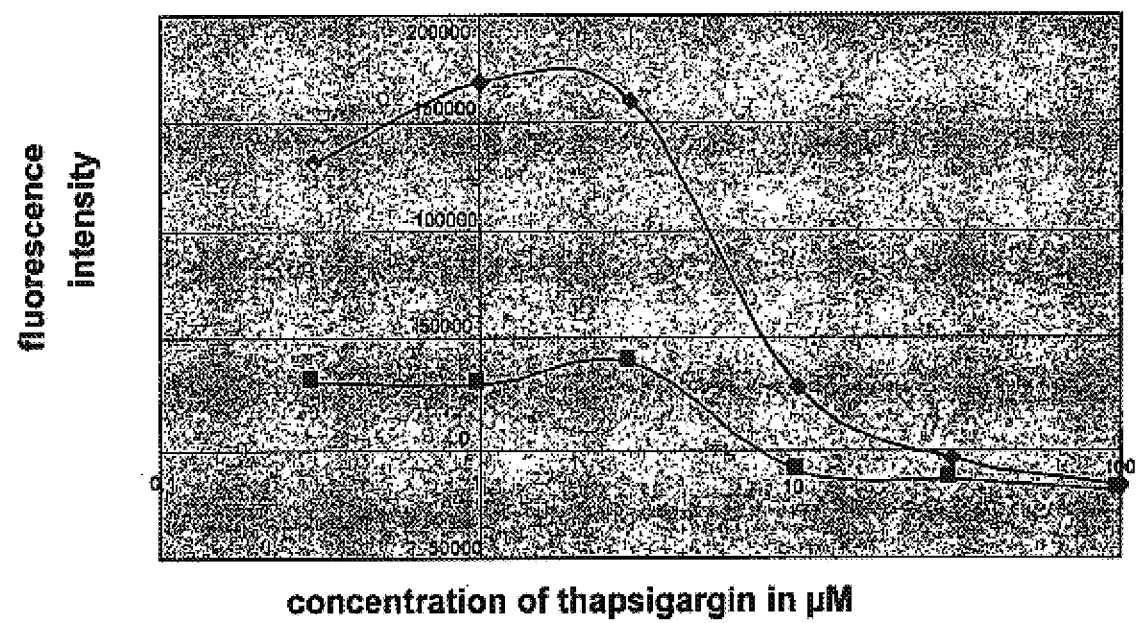
FIG. 6 shows a dose-response curve for thapsigargin showing the enhancer effect at high concentrations and the inhibitor effect at high concentrations.
Figure 17:
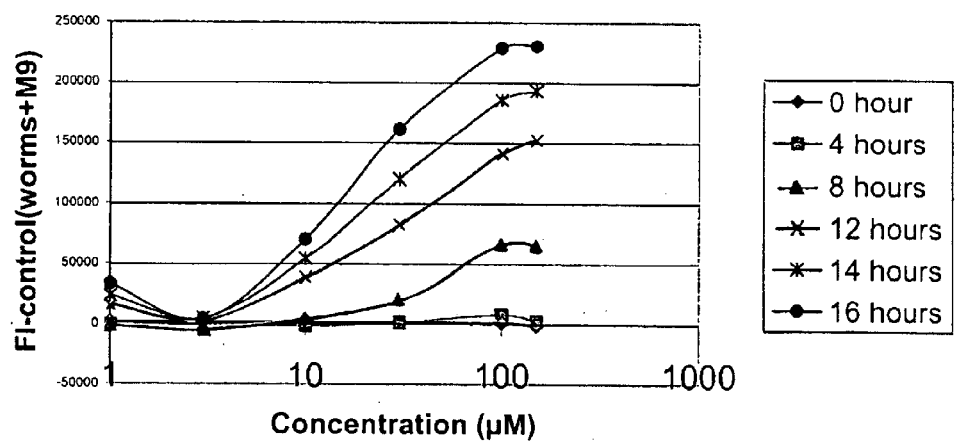

The egg laying assays and the mating assays are based on the measurement of the eggs and the offspring. In certain embodiments, the quantity of eggs can be measured by applying specific antibodies to the eggs, and counter staining with dyes specific to the antibodies which recognize the eggs as known in the art. In further embodiments, the methods may comprise detecting the numbers of eggs produced with the use of specific dyes which recognize the eggshell. In one specific embodiment detection of the number of eggs in a well is carried out using a dye which recognizes a substance released on hatching of the eggs. During the hatching process the enzyme chitinase is released into the medium. The enzyme recognizes the substrate 4-methylumbelliferyl $^2$-D-N,N,N,-triacetylchitotrioside (or 4-Methylumbelliferyl $\beta$-$_D$-N,N'-diacetylchitobioside) which is a fluorescent precursor molecule (provided by Sigma, St. Louis, Mo.). Hydrolysis of the synthetic substrate 4-methylumbelliferyl triacetylchitotrioside is followed by measuring the fluorescence of the liberated 4-methylumbelliferone in a microtiter plate reader. Other substrates which comprise a dye, which may be a luminescent, fluorescent or coloured dye, linked to a chitin moiety may be used in such screen. An example of this is Resorufin N-acetyl-$^2$-glucosaminide or CM-DCF-NAG provided by Molecular Probes, Eugene, OR, or provide by Sigma. Egg laying assays using chitinase substrates may be carried out using the following general methodology:

Place 30 nematodes in a microtiter plate in 80 µl of M9 medium. Add the compound to be tested at appropriate concentrations in 10 µl. Add the chitinase substrate at an appropriate concentration in 10 µl. Measure fluorescence, luminescence, or colour formation at various time intervals. Results of typical experiments are shown in FIGS. 6 and 17, clearly indicating that increasing the time interval results in better readouts.

In a still further embodiment of the invention the step of detecting a signal indicating a phenotypic, physiological, behavioural or biochemical change in the nematode worms using non-visual detection means comprises detecting a change in the defecation behaviour of the nematode worms.

Defecation in nematodes such as C. elegans is achieved by periodically activating a stereotyped sequence of muscle contractions. These contractions are started in the anterior body wall muscles. At the zenith of the anterior body contractions the four anal muscles also contract. The four anal or enteric muscles are the two intestinal muscles, the anal depressor and the anal sphincter. In addition to this series of muscle contractions, specific neurons are also involved in the regulation of defecation, including the motor neurons, AVL and DVB. Since defecation requires the activity of both muscles and neurons high-throughput screening assays can be developed which use a read-out based on detection of changes in the defecation behaviour of nematodes such as C. elegans. Again, assays based on detection of defecation can be used for the same purposes as the pharynx pumping and movement assays described herein.

The defecation assay is preferably performed using C. elegans mutants which have a defective defecation behaviour and particularly with C. elegans mutants which are constipated. Several mutants with all kinds of defects in the defecation cycle have been reported (Thomas, Genetics 124: 855–872, 1990; Iwasaki et al., PNAS 92: 10317–10321, 1995; Reiner et al., Genetics 141: 961–976, 1995). However, the defecation assay can also be performed using wild-type worms or worms with no defecation defects which allow screening for compounds which are inhibitors of defecation. As defecation in C. elegans requires the activity of muscles and neurons, compounds which alter the rate of defecation may potentially have CNS-related pharmacological activity.

The rate of defecation of nematodes such as C. elegans can be easily measured using a marker molecule which is sensitive to pH, for example the fluorescent marker BCECF. This marker molecule can be loaded into the C. elegans gut in the form of the precursor BCECF-AM which itself is not fluorescent. If BCECF-AM is added to the medium in the wells of the multi-well plate the worms will take up the compound which is then cleaved by the esterases present in the C. elegans gut to release BCECF. BCECF fluorescence is sensitive to pH and under the relatively low pH conditions in the gut of C. elegans (pH<6) the compound exhibits no or very low fluorescence. As a result of the defecation process the BCECF is expelled into the medium which has a higher pH than the C. elegans gut and the BCECF is therefore fluorescent. The level of BCECF fluorescence in the medium (measured using a multi-well plate reader on settings Ex/Em=485/550) is therefore an indicator of the rate of defecation of the nematodes.

Defecation can also be measured using a method based on the luminescent features of the chelation of lanthanides such as terbium in the presence of an aromatic group, such as aspirin. The method requires two pre-loading steps, first the wells of a multi-well plate are pre-loaded with aspirin conjugated to a chelator such as DTPA (prior to the addition of the nematode worms) and second, bacteria or other nematode food source particles are pre-loaded with terbium using standard techniques known in the art. C. elegans are then placed in the wells pre-loaded with aspirin conjugated to a chelator such as DTPA and are fed with the bacteria pre-loaded with terbium.

The terbium present in the pre-loaded bacteria added to the wells will result in a low level of background luminescence. When the bacteria are eaten by the nematodes the bacterial contents will be digested but the terbium will be defecated back into the medium. The free terbium will then be chelated by the aspirin which was pre-loaded into the wells resulting in measurable luminescence. The luminescence thus observed is therefore an indicator of nematode defecation.

A further method to detect defecation is based on esterified chelators of lanthanides. This method is essentially the similar to the method described above to detect defecation by aspirin chelation of Terbium. The main advantage of the lanthanide chelation method is that the chelator does not to be coated on the wells, but can be added to the liquid medium in which the nematode is placed.

Lanthanides are rare earth metals that are known to exhibit a long lifetime fluorescence when chelated in presence of an aromatic group. Well known lanthanides are Europium and Terbium; a typical chelator is diethylenetriaminepentaacetic acid (DTPA). The assay is based on the principle that an esterified DTPA cannot chelate terbium. After ingestion by *C. elegans* such esterified chelator will be processed by gut esterases. Upon release by defecation it will readily chelate terbium, thus allowing detection using time-resolved fluorescence, as known in the art This method allows the detection of very small amounts of material. When adapted to a short incubation time, the method may allow monitoring of defects in the defecation process.

The invention will be further understood with reference to the following experimental examples together with the accompanying Figures.

FIG. 1 is an overview of the neurons and transmitters that are known to have a direct influence on the pumping rate of the *C. elegans* pharynx.

Figure 2:
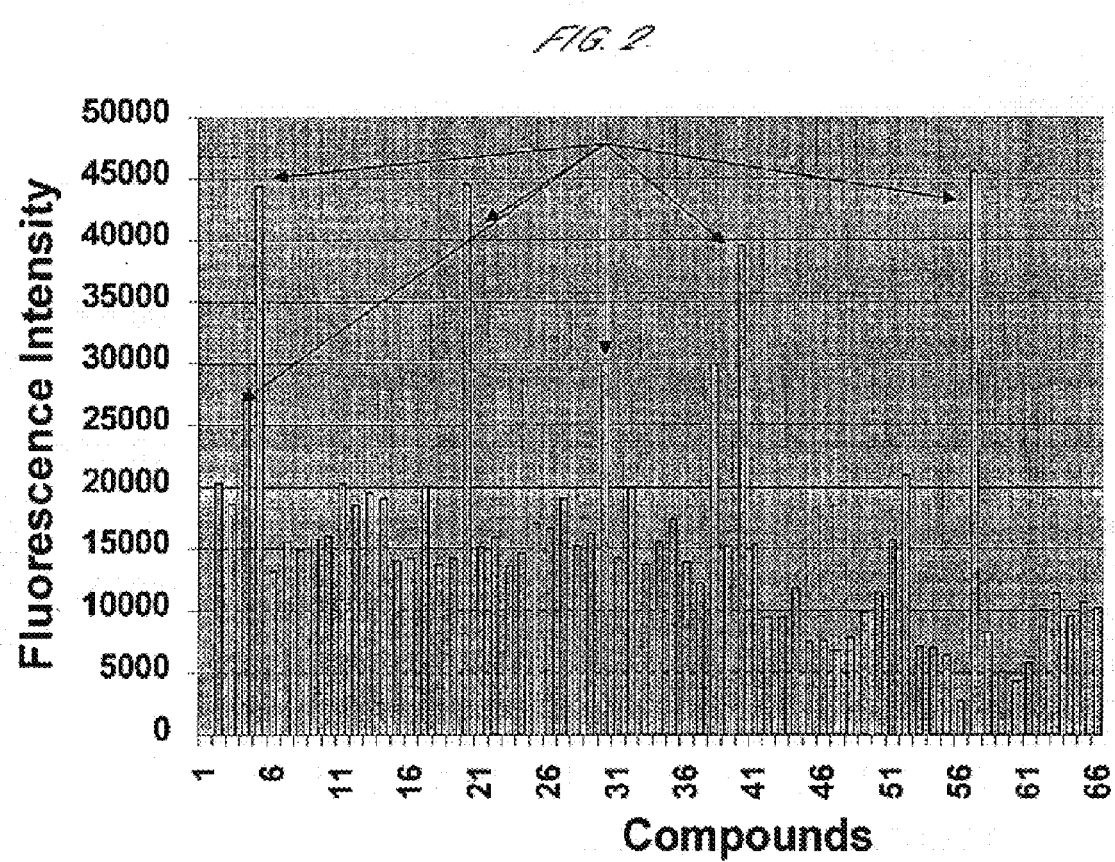
FIG. 2 shows an example of the detection of enhancers of the pumping rate of the C. elegans pharynx, using a fluorescent read-out.

FIG. 2 shows an example of the detection of enhancers of the pumping rate of the *C. elegans* pharynx, using a fluorescent read-out.

Figure 3:
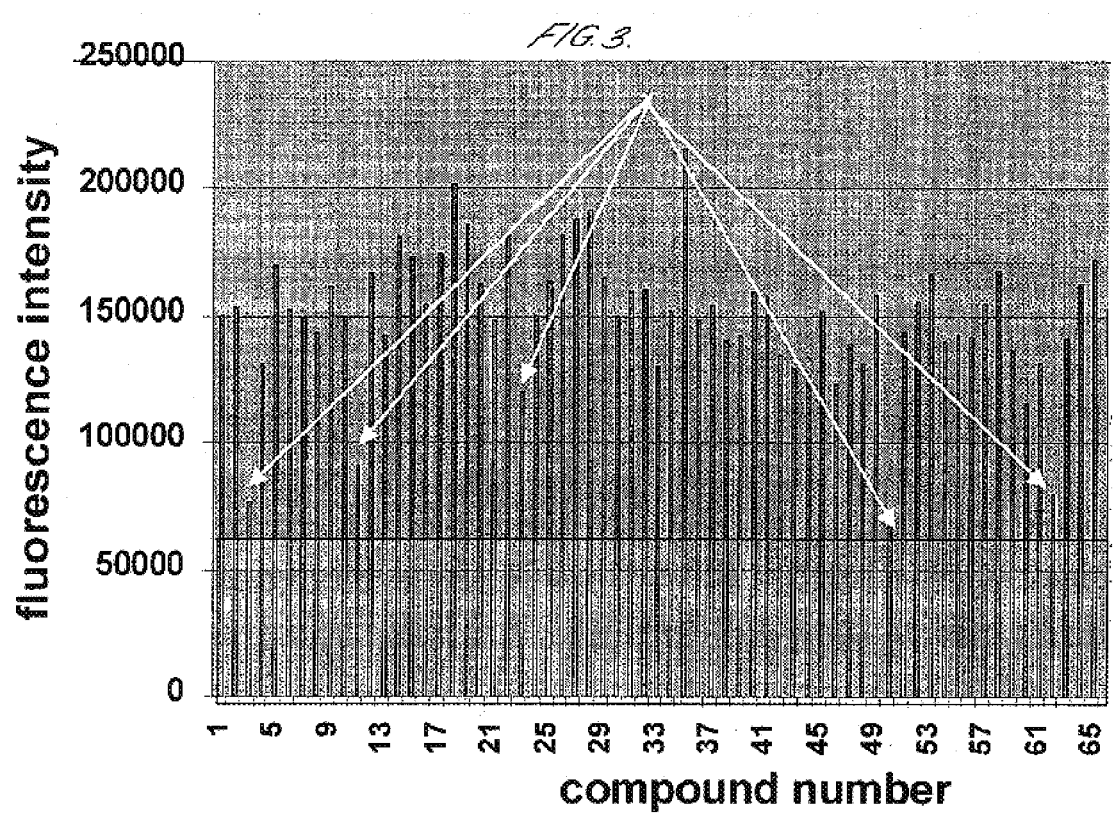
FIG. 3 shows an example of the detection of inhibitors of the pumping rate of the C. elegans pharynx, using a fluorescent read-out.

FIG. 3 shows an example of the detection of inhibitors of the pumping rate of the *C. elegans* pharynx, using a fluorescent read-out.

FIG. 4 shows dose-response curves for the inhibitors tamoxifen, BP554 and pimazide.

Figure 5:
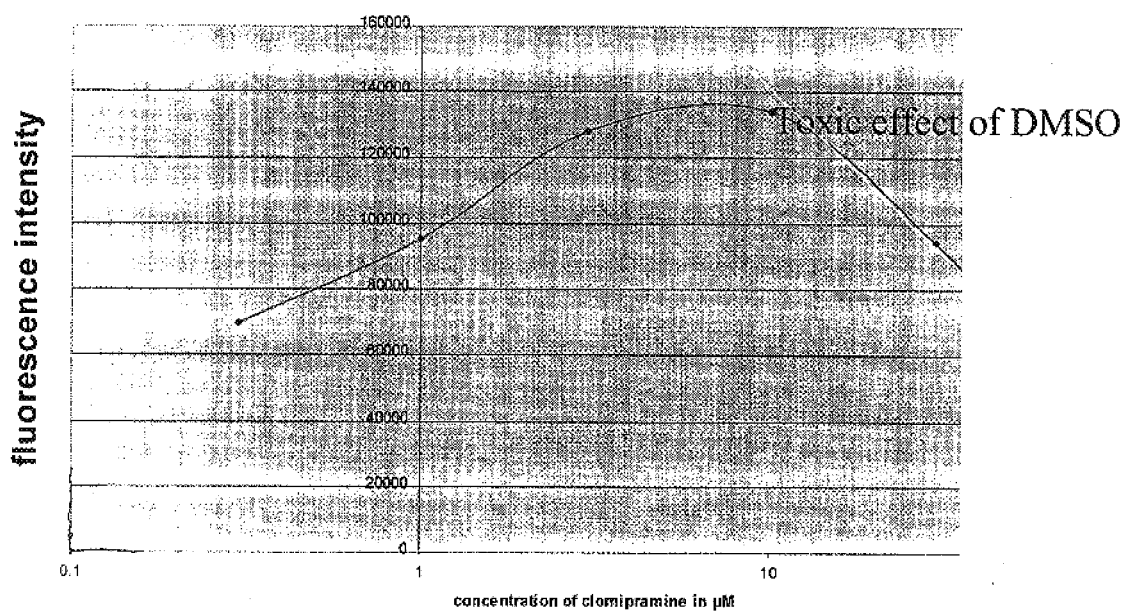
FIG. 5 shows a dose-response curve for the enhancer clomipramine, showing the toxic effect of DMSO.

FIG. 5 shows a dose-response curve for the enhancer clomiprarnine, showing the toxic effect of DMSO.

FIG. 6 shows a dose-response curve for thapsigargin showing the enhancer effect at high concentrations and the inhibitor effect at high concentrations.

Figure 7:
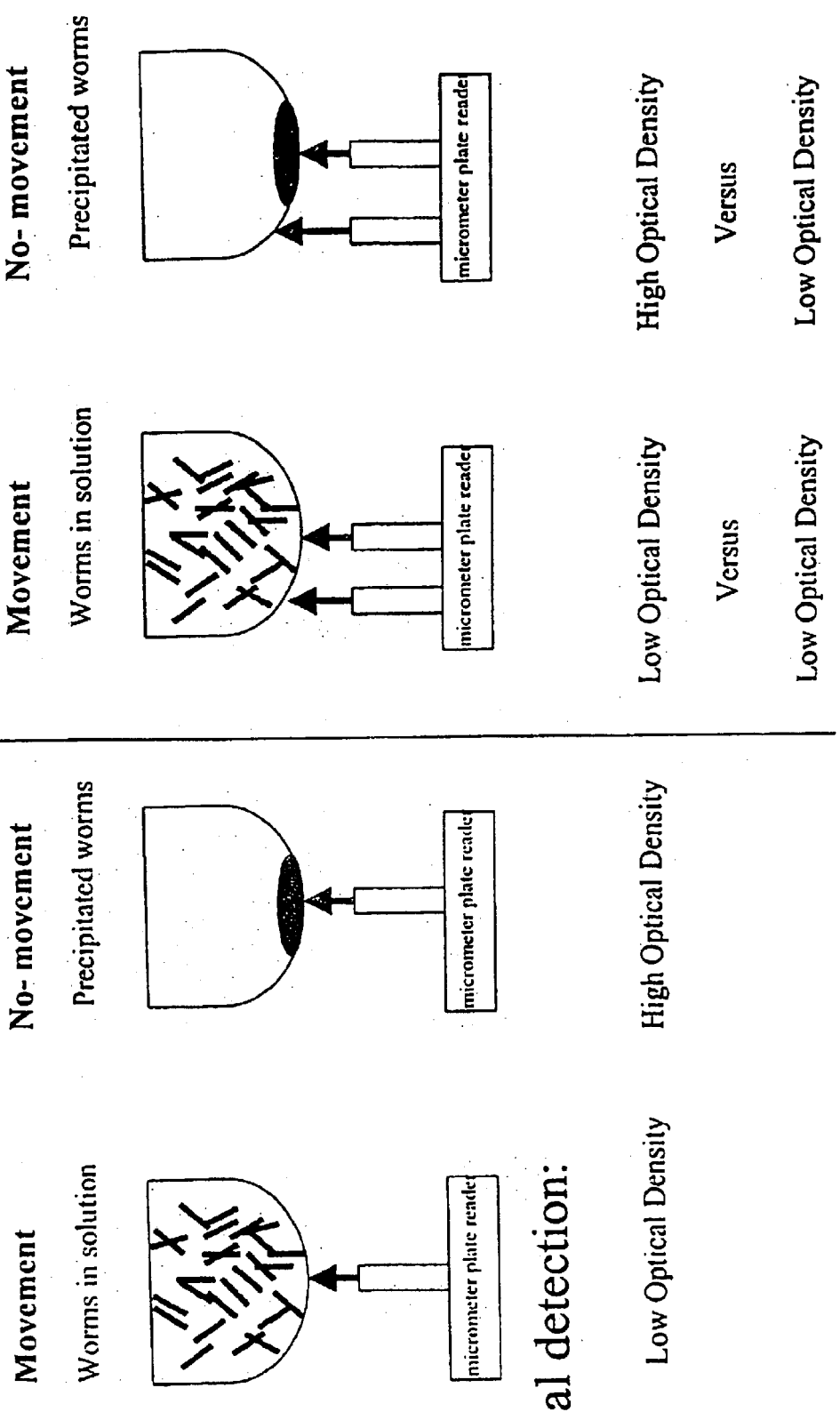
FIG. 7 illustrates the principle of the movement assay.

FIG. 7 illustrates the principle of the movement assay.

Figure 8:
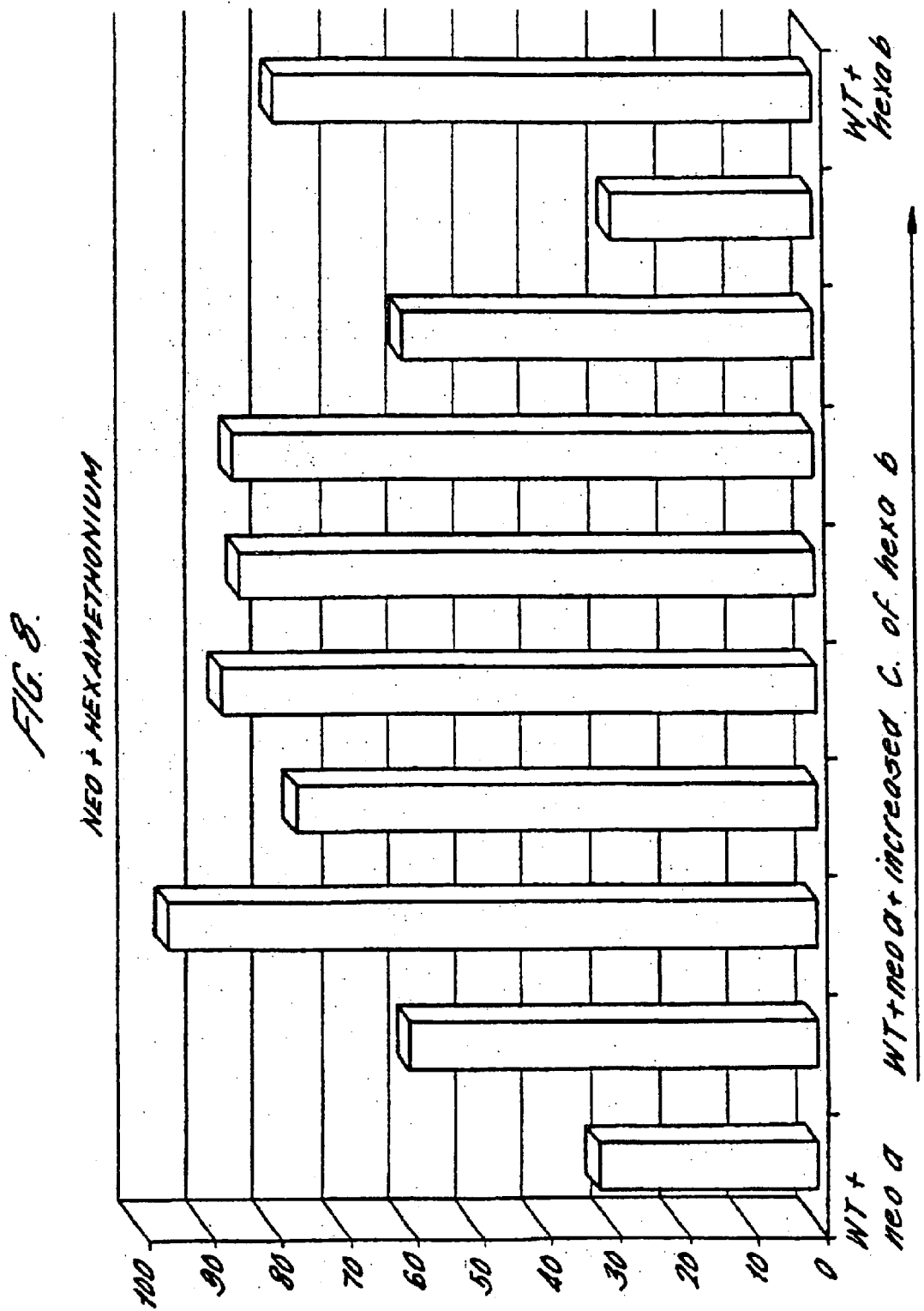
FIG. 8 illustrates the principles of chemical substrate selection and antagonist selection using the movement screen.

FIG. 8 illustrates the principles of chemical substrate selection and antagonist selection using the movement screen.

Figure 9:
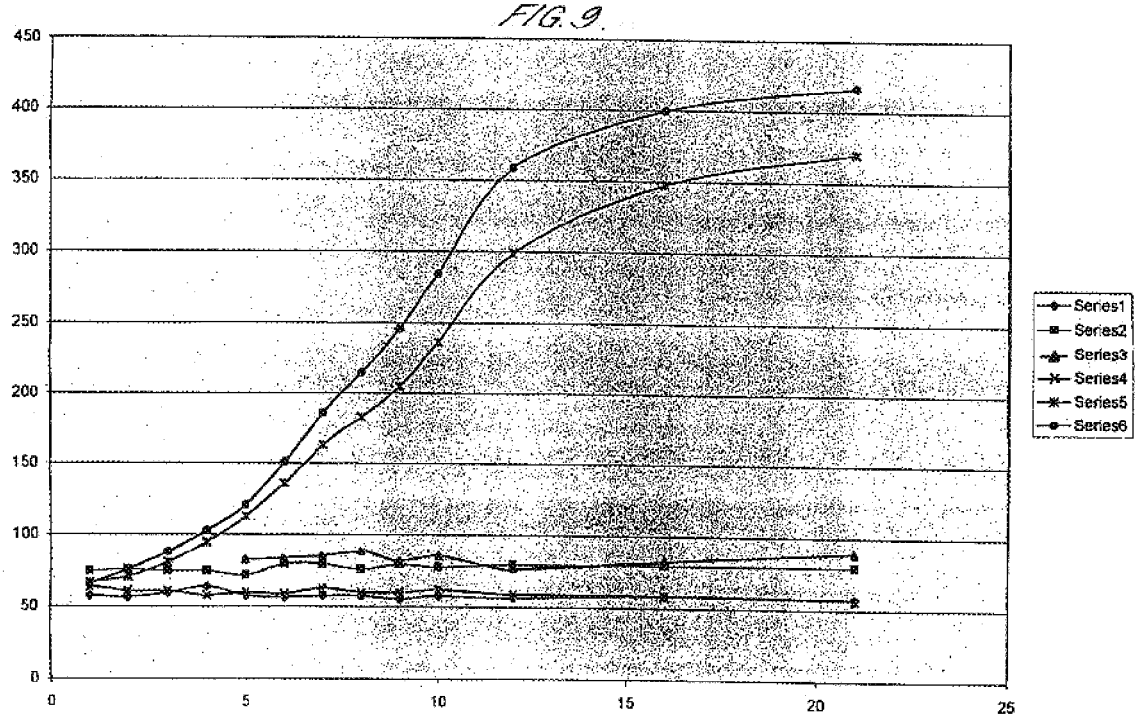
FIG. 9 shows the results of a representative movement assay illustrating the change in nematode autoflourescence (y-axis) with time (x-axis).

FIG. 9 shows the results of a representative movement assay illustrating the change in nematode autofluorescence (y-axis) with time (x-axis).

Figure 10:
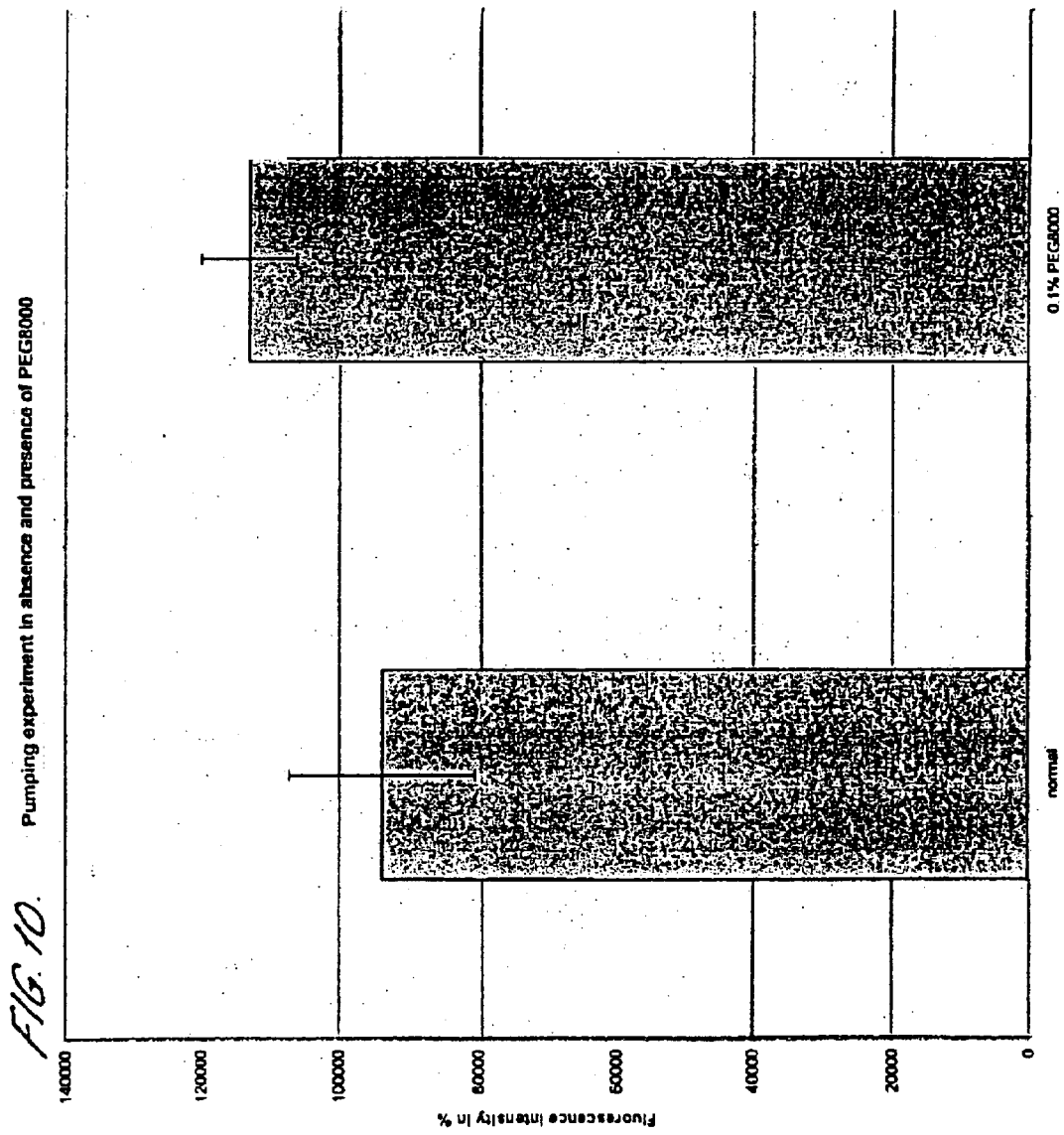
FIG. 10 illustrates the result of an experiment to show the effect of PEG8000 on performance of the pharynx pumping assay. 100 worms (strain HD8) were incubated for 3 hours in the presence of $0.5\mu M$ calcein-AM. They were handled with or without the addition of 0.1% PEG.

FIG. 10 illustrates the result of an experiment to show the effect of PEG8000 on performance of the pharynx pumping assay. 100 worms (strain HD8) were incubated for 3 hours in the presence of 0.5 $\mu$M calcein-AM. They were handled with or without the addition of 0.1% PEG.

Figure 11:
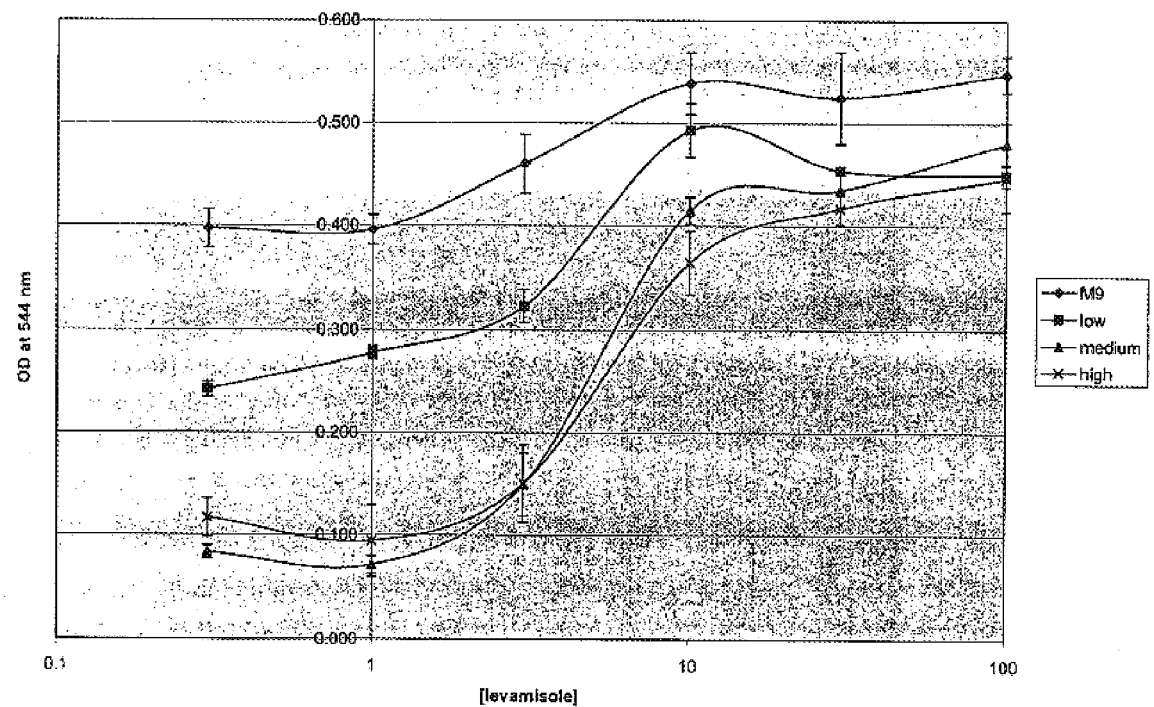
FIG. 11 illustrates the results of experiment to show the effect of viscosity of the medium on performance of the movement assay.

FIG. 11 illustrates the results of experiment to show the effect of viscosity of the medium on performance of the movement assay.

FIG. 12 and FIG. 13 illustrate the effect of viscosity of the medium on performance of the movement assay for various *C. elegans* mutants in a comparative study. 100 worms were incubated in a round bottom shaped microtiter plate. OD was measured at 340nm in various viscous media (M9, medium viscosity carboxymethylcellulose and high viscosity carboxymethylcellulose). Measurements were done in triplicate.

Figure 14:
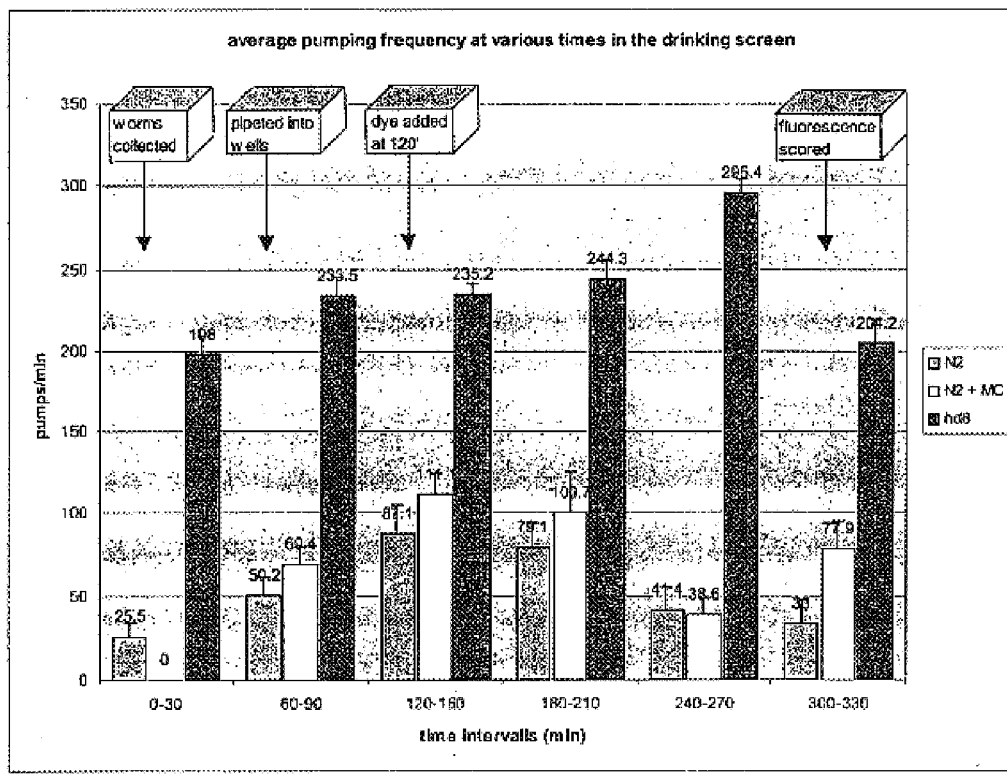
FIG. 14 and FIG. 15 illustrate the effect of viscosity of the medium on the pharynx pumping screen. N2+MC denotes wild-type worms in medium containing carboxymethylcellulose.
Figure 15:
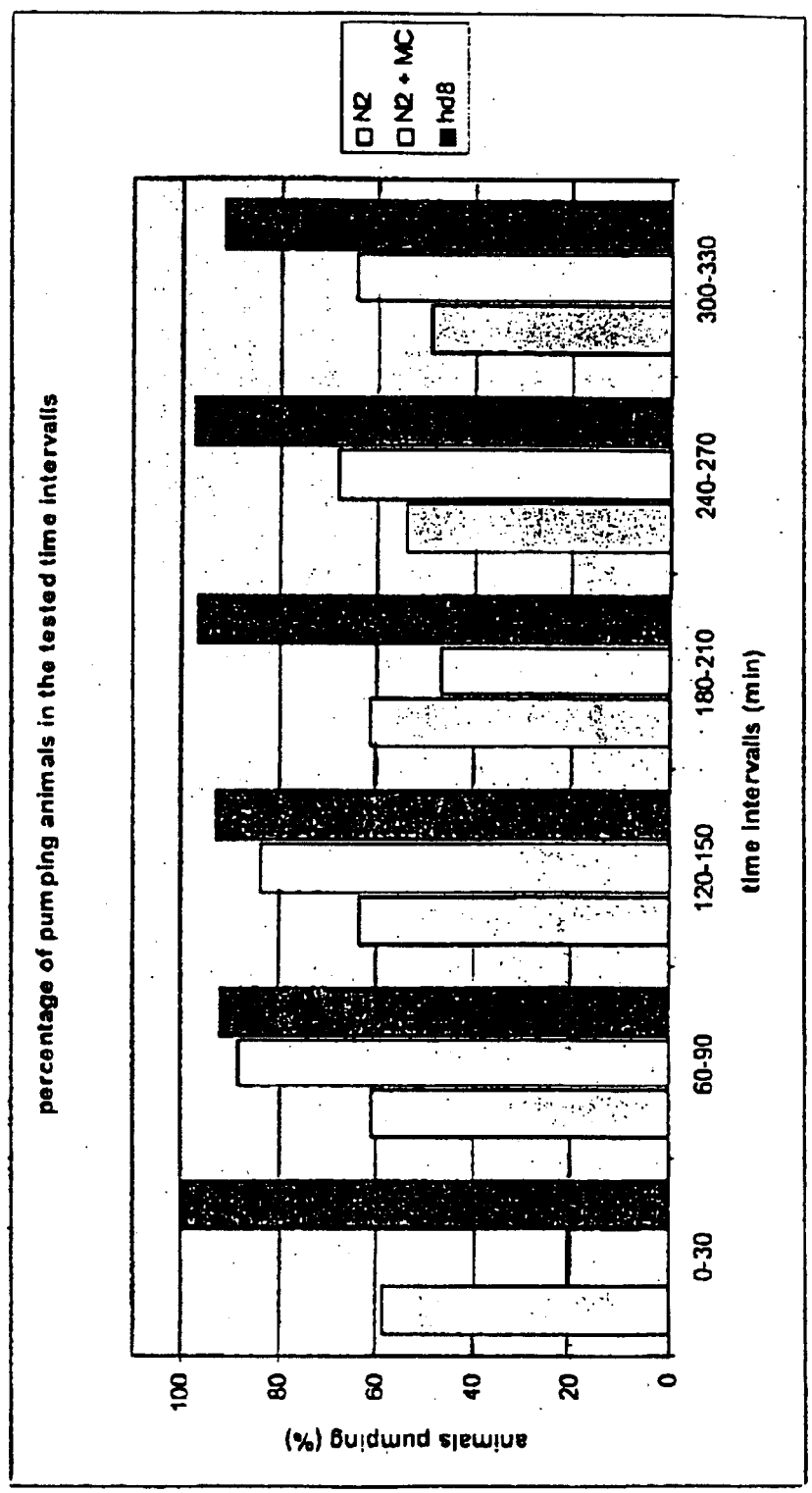

FIGS. 14 and 15 illustrate the effect of viscosity of the medium on the pharynx pumping screen. N2+MC denotes wild-type worms in medium containing carboxymethylcellulose.

Figure 16:
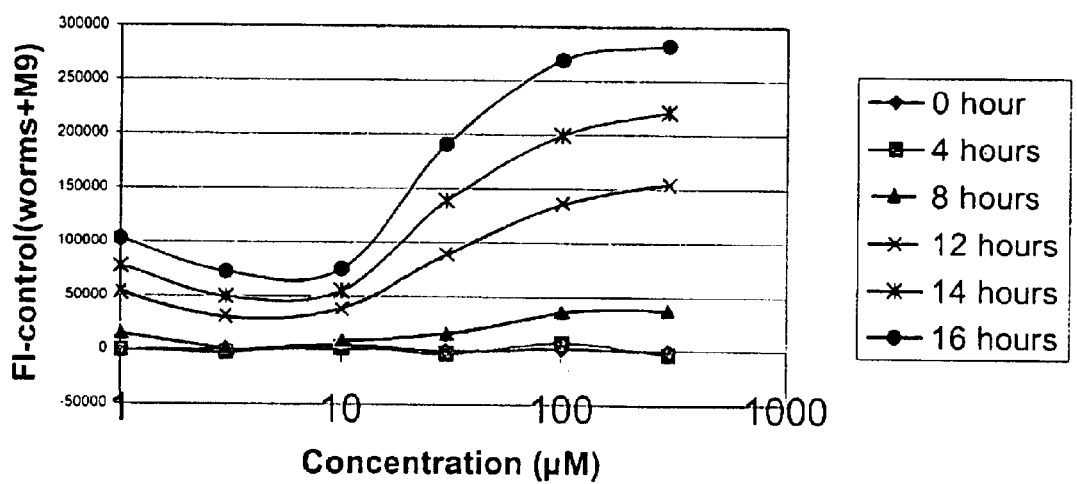
FIG. 16 and FIG. 17 illustrate the kinetics of egg laying assays using N2 worms based on detection of chitinase activity using a fluorescent substrate. The assays were carried out in the presence of varying concentrations of clomipramine and fluoxetine, respectively.

FIGS. 16 and 17 illustrate the kinetics of egg laying assays using N2 worms based on detection of chitinase activity using a fluorescent substrate. The assays were carried out in the presence of varying concentrations of clomipramine and fluoxetine, respectively.

Figure 18:
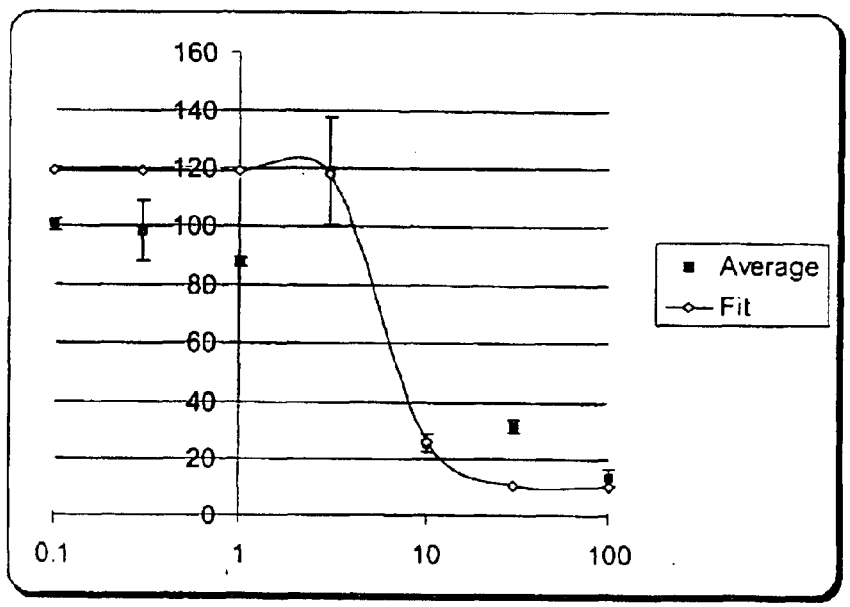
FIGS. 18 to 21 illustrate the effect of compounds of known insecticidal activity on the pharynx pumping rate of C. elegans.
Figure 19:
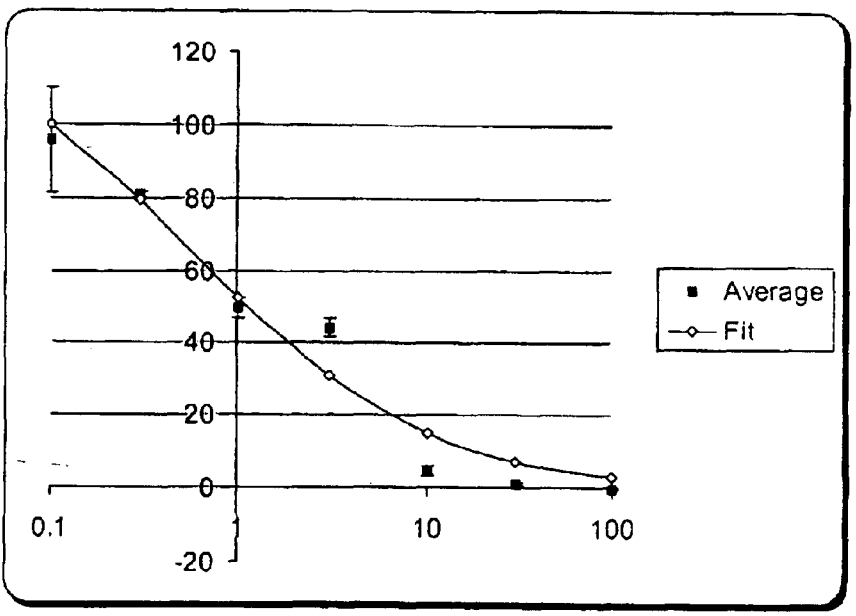
Figure 20:
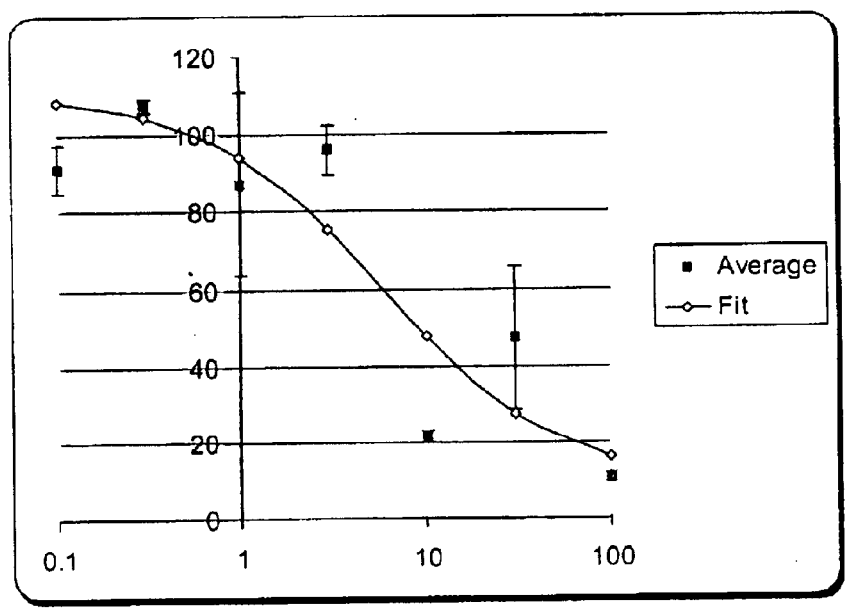
Figure 21:
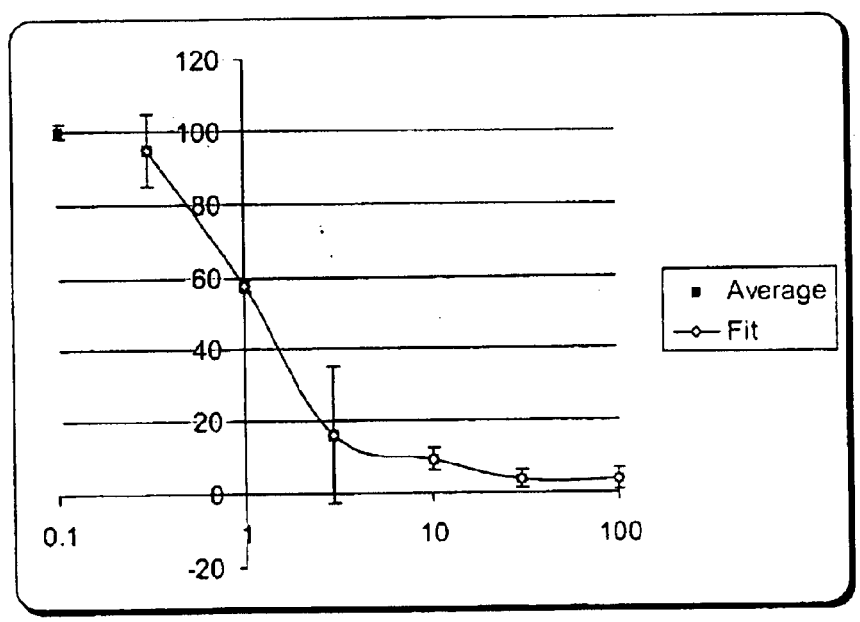

FIGS. 18 to 21 illustrate the effect of compounds of known insecticidal activity on the pharynx pumping rate of *C. elegans*. FIG. 18-Picrotoxin, FIG. 19-Rotenone, FIG. 20-Dieldrin, FIG. 21-Ivermectin. A reduction in the pharynx pumping rate on exposure to insecticide is clearly seen.

EXAMPLE 1

Distribution of Nematodes, and Dilution of Compounds

The basic protocol for performing a screen using the method of the invention is described for multi-well plates with 96 wells, but other multi-well plates with 6, 12, 24, 3 84 or 1536 wells could be used.

Preferentially, synchronized worms are used. The production of large amounts of synchronized worms has been described in (Methods in cell biology, Vol. 48, ibid). After the worms have grown to the preferred stage, they are washed in M9 buffer prior to further use, and re-suspended in an assay buffer (40 mM NaCl, 6 mM Kcl, 1 mM $CaCl_2$, 1 mM $MgCl_2$). (10×M9 buffer: 30 g $KH_2PO_4$, 60 g $Na_2HPO_4$, 50 g NaCl, 10 ml MgSO4 1M, made up to 1 liter with $H_2O$). Other buffers than M9 buffer can be suitable for this purpose.

The worms are then diluted and resuspended in semi-soft agar (final concentration of 0.25% low melting agarose in M9 buffer). This procedure results in an equal, homogenous and stabilised suspension of the nematodes. Other polymers than low melting agarose can be used in this procedure. The presence of a homogenous worm suspension facilitates the equal distribution of the worms in the multi-well plates, but is not essential for the described screening assay. Any other method that results in a homogenous distribution of the nematodes worms over the wells will be useful. More specifically, the use of a worm dispenser will result in even a better, and hence a more equal distribution of the worms over the wells of the multi-well plate.

The worms are distributed in the multi-well plates using electronic 8 channel pipettes. In a preferred set-up of this experiment 40+/−5 worms are added to every well of the microtiter plate.

The chemical substances are made soluble in DMSO. Any other solvent can be used for this purpose, but most selected chemical substances appear to be soluble in DMSO.

The chemical substance is added in the wells at various concentrations but preferentially a concentration between 3 to 30 $\mu$M is chosen as this gives the clearest results. It possible to screen for dosage effects by varying the concentration of the chemical substance from less than 1 $\mu$M up to 100 $\mu$M.

The concentration of the DMSO should not be too high and preferentially should not exceed 1%, more preferentially the concentration of the DMSO should not exceed 0.5% and even more preferentially, the concentration of the DMSO is lower than 0.3%.

EXAMPLE 2

Conditions for a Pharynx Dumping Assay

Depending on the specific assay which it is desired to perform, different *C. elegans* strains can be used. Screens to select for chemical substances inhibiting the pumping rate of the *C. elegans* pharynx are generally performed with mutant *C. elegans* strains which have a constitutively pumping pharynx. Wild-type worms can also be used in this screen, but the mutants worms are preferred. Other *C. elegans* mutants can be used in this screen to select for inhibitors of pumping. The selected mutant C. elegans with the constitutively pumping pharynx pumps medium into the gut at a constant rate and reduction/rescue of this phenotype can easily be scored, which facilitates the detection and selection of chemical substances.

To select for chemical substances that enhance the pumping of the C. elegans pharynx the screen is generally performed using wild-type C. elegans worms but other mutants could be used in this screen. A wild type worms will not pump or show a reduced pumping rate in liquid medium that doesn't contain any food source as the food source is one of the signals to induce pharynx pumping. As wild-type worms show a reduced pumping rate in this assay, enhancement of the pumping rate can easily be scored.

The pumping rate of the pharynx is measured indirectly by adding a marker molecule precursor such as calcein-AM to the medium and measuring the formation of marker dye in the C. elegans gut. Calcein-AM is cleaved by esterases present in the C. elegans gut to release calcein, which is a fluorescent molecule. The pumping rate of the pharynx will determine how much medium will enter the gut of the worm, and hence how much calcein-AM will enter the gut of the worm. Therefore by measuring the accumulation of calcein in the nematode gut, detectable by fluorescence, it is possible to determine the pumping rate of the pharynx.

Chemical substances that alter the pumping rate of the pharynx will result in more or less uptake of the calcein-AM and hence in more or less fluorescent signal. Moreover, using a multi-well plate reader, the fluorescence can be measured rapidly and quantitatively, resulting in a fast, quantitative high throughput screening method for the identification of chemical substances with potential pharmacological activity.

To perform the pharynx pumping screen with calcein-AM, a concentration of between 1 and 100 $\mu$M calcein-AM is added into the medium. Preferably 5 to 10 $\mu$M calcein-AM is used. Fluorescence is measured using a multi-well plate reader (Victor2, Wallac Oy, Finland) with following settings: Ex/Em=485/530.

This measurement of the pharynx pumping rate by detecting the accumulation of a marker molecule is not limited to calcein-AM. Other precursors can be used and thus the assay as described here can be changed to be suitable for other precursors. The precursor can be cleaved by esterases, but could also be a substrate for other enzymes in the nematode gut. Furthermore, the marker molecule should not necessary be a fluorescent molecule, but can be a molecule detectable by other methods. Most of these precursor substances are commercially available or could be synthesized according to methods known in the art. Some examples are:

With a fluorescent read out:
Esterases substrates: Calcein-AM, FDA, BCECF-AM
Alkaline phosphatase substrates: Fluorescein diphospate (FDP)
Endoproteases; Aminopeptidase substrates: CMB-leu
With a luminescent read out:
alkaline phosphatase substrates: AMPPD
With a colour read out.
Glucuronidase substrates: X-gluc Other target enzymes present in the gut for which substrates can be found or developed are DNAses, ATPases, lipases and amylases. An overview of various marker molecules, mainly fluorescent can be found in AHandbook of fluorescent probes and research chemicals, molecular probes, ed. by R. P. Haughland"

EXAMPLE 3

Testing the Pharynx Pumping Assay with Compounds from the Pharmacopoeia 160 well known drugs selected from the pharmacopoeia were used in a screen to test the performance of the pharynx pumping method. The drugs tested belong to a variety of categories, which included analgesics, antidiabetics, antiarrythmics, calcium channel blockers, diuretics, cholinesterase inhibitors, proton pump inhibitors and antidepressants.

The drugs were randomly distributed over the wells of two 96-well multi-well plates. The pumping rate of the C. elegans pharynx was measured using calcein-AM as described in Example 2. C. elegans wild-type strain N2 was used to select for enhancers of the pumping phenotype, and a mutant C. elegans strain with a constitutively pumping pharynx was used to detect inhibitors of pumping.

In a first assay, the substrate calcein-AM was added to the medium at the same time as the worms and the compounds. The fluorescence was measured after approximately one hour.

In a variation of this protocol, compounds and worms are added to the medium first and incubated for approximately 1 hour. After this incubation period that allowed for the chemical substances to activate or to inhibit the pumping rate of the pharynx, calcein-AM was added. The plates where then further incubated for one hour prior to fluorescence measurement in the microtiter plate reader.

Although a broad range of chemicals have been selected from the pharmacopoeia with a variety of actions, most if not all of the compounds that had an activity on the pharynx pumping rate belong to the family of CNS drugs, calcium channel inhibitors and muscle relaxants, indicating that the C. elegans pharynx assay is a good model system to screen for compounds that have activity in the above described areas.

The variation of the protocol resulted in the detection of some new compounds, next to the compounds that have previously been detected; these include the chemicals metrifonate, physostigmine, atropine, L-Hyoscyamine, diphenylhydantoin and ZAPA. All these compounds are known as CNS drugs or are used to treat Alzheimer's disease or are used as antipsychotic, antidepressant or antiepileptic drugs.

EXAMPLE 4

Selecting for the Mode of Action of a Compound and Selecting Compounds which Act on Specific Targets Amongst 14 types of pharyngeal neurons, at least the neurons, 11, 12, 13, M3, MC, NSM, M1, RIP and M4 have been shown to be important for pharynx pumping, The neurons MC, M3, M4 and NSM are known to regulate the contraction/pumping rate of the pharynx. They control respectively the rate of pumping, timing of muscle relaxation, isthmus peristalsis and the perception of food. The main neurotransmitters involved in neuronal signal transduction in the nematode C. elegans are acetylcholine and serotonin, glutamate, octopamine, dopamine and GABA (The nematode Caenorhabditis elegans ed. by W. B. Wood et al., CSHL press 1988, page 337–392).

From the drugs selected in the basic pharynx screen (Example 3) it is clear that the pharynx pumping rate is influenced by inhibitors and agonists of neurotransmitters, and by compounds that inhibit or enhance neurotransmitter pathway calcium channels, sodium/calcium channels, chloride channels. These chemical substances are used in a very wide range of prescribed drugs, such as anti-depressants, anti-psychotics, anxiolytics, tranquillizers, antiepileptics, muscle relaxants, sedatives, anti-migraine drugs, analgesics and hypnotics. Some of these Central Nervous System (CNS) related drugs have applications in disease areas such as CNS related genetic diseases as Parkinson's disease and Alzheimer's disease.

To overview the present CNS related drugs, it is best to classify them according to their biochemical function in the neurotransmitter pathway cascade. In brief, CNS related drugs can at least have influence on the following features of the pathway:

- A CNS drug can have influence on the precursor compounds, or can be precursor molecule for the synthesis of a neurotransmitter.
- A CNS drug can enhance, inhibit or modulate the synthesis of a neurotransmitter
- A CNS drug can have a function in the depletion of the transmitter.
- A CNS drug can prevent or stimulate the release of the transmitter from the synaptic vesicles in the synaptic cleft.
- A CNS drug can function as a receptor inhibitor or stimulator.
- A CNS drug can mimic the transmitter.
- A CNS drug can function as conduction inhibitor or activator.
- A CNS drug can function as an activator or inhibitor of the conduction blockade.
- A CNS drug prevent or stimulate the re-uptake of transmitter after firing of the neuron.
- A CNS drug can functions as a false transmitter (−/+).

Next to these features that are all related to the neurotransmitter pathways, a lot of CNS related drugs can be found in the classes of chloride channel blockers, sodium/calcium channel blockers, calcium blockers, and other ion channel blockers.

To screen for CNS related drugs, several "in vitro" screening assays have been developed in the prior art. These screening methods, designated as "in vitro binding assays" or "cloned transporter assay systems" are well known to persons skilled in the art. For these assays, cell membranes harboring a specific type of receptor are isolated from mammalian tissue or specific tissue cultures. In most cases these membranes are isolated from cells that over-express the desired receptor. Depending on the type of receptor that is present in the membrane, neurotransmitters such as acetylcholine, dopamine, serotonin, glutamate, GABA and octopamine, but also hormonal substances such as norepinephrine, adrenaline and others are the subject of the screening assay. When the receptor ligand (being the neurotransmitter in most cases) is radioactive labelled, it is possible to measure the binding rate of the ligand to the receptor. Experimental conditions can then be set-up that compare the binding rate of the radioactive ligand to the receptor. Putative CNS drugs and other chemical substances can then be isolated that alter the binding of the ligand to the receptor. Several variations of this methodology have been developed, some of which are able to isolate compounds that inhibit re-uptake of the ligand such as serotonin, norepinephrine and dopamine (Koppel et al., Chem. Biol. 1995, Jul. 2:7 483–7; Beique et al., Eur. J. Pharmacol. 1998, May 15 349:1 129–32) Other systems that have been developed for the screening of CNS related drugs involve isolated tissues or organs from mammals. Furthermore systems have been described to isolate CNS related drugs, with living animals such as mice.

Although these screening assays can be used to isolate antagonists of neurotransmitters, these "in vivo" assays do not reflect the in vivo effect of the isolated compound, as only the association with the desired receptor is monitored. Moreover for every potential target in the neurotransmitter pathway cascade, an "in vitro binding assay" needs to be developed. Furthermore, for some of the putative targets for CNS related drugs as described above, no assays have been developed or these assays are difficult to develop, or no high throughput screening is possible. All known assays with tissue and animal models also suffer from the latter problem. Moreover the assays using animal tissues or organs involve the killing of large amounts of animals, and screening methods based on the use of higher animals, especially mammals, are increasingly to be avoided due to issues of animal welfare.

The pharynx pumping assay methodology can be used to determine in which neurotransmitter pathway a compound shows activity (acetylcholine, dopamine, serotonin, glutamate, octopamine, GABA, etc.). Furthermore it is possible to determine the mode of action of newly isolated chemical substances and screen selectively in a certain pathway for chemical substances with potential pharmacological activity.

A collection of *C. elegans* nematode mutants have been constructed which are defective in one or more genes. The defect can be introduced stably by standard technology (i.e. gene knock-outs) but can also be transiently introduced by RNAi technology. Both techniques are well known in the field of *C. elegans* genetics. The genes that are affected in the nematodes of this collection are genes that are those involved in one or more neurotrasmitter pathways. Examples of affected genes are genes that code for neurotransmitter receptors such as muscarinic receptors, glutamate receptors, hormone receptors, 5-HT receptors, cannabinoid receptors, adrenergic receptors, dopaminergic receptors, opioid receptors, GABA receptors, adenosine receptors, VIP receptors, nicotinic receptors, proteins involved in neurotransmitter synthesis or neurotransmitter release pathways and G-protein coupled receptors, genes encoding proteins for G-protein coupled second messenger pathways such as adenylate cyclase, protein kinase A, cAMP responsive element binding proteins, phospholipase C, genes encoding for functions in gap junctions and genes encoding for ion channels and ion pumps.

These mutants are tested in a pharynx pumping screen as described in the previous Examples and the results are stored for reference. Compounds having an unknown mode of action are then tested in the pharynx pumping screen and the results obtained compared with the reference results obtained from the mutants in order to determine the mode of action or pathway of the compound.

In addition to these mutants, transgenic worms have also been constructed. *C. elegans* can be engineered to express human genes using standard technology (described in Methods in Cell Biology, vol. 48). Once again, both transient and stable transgenic nematodes can be constructed, and the methods for engineering the expression of heterologous and homologous transgenes in the nematode *C. elegans* are well known within the field. These transgenes can be expressed solely in cells of the pharynx with the use of pharynx-specific promoters, but could also be expressed solely in the neurons affecting the pumping rate of the pharynx.

To screen for and to isolate chemical substances that are active in the area of CNS related drugs, the transgenes expressed in the transgenic *C. elegans* can encode neurotransmitter receptors such as muscarinic receptors, glutamate receptors, hormone receptors, 5-HT receptors, neurotransmitter synthesis, neurotransmitter release pathways and G-protein coupled receptors. These transgenes can be protein encoding sequences of human origin. At least 400 G-protein coupled receptors have been sequenced so far.

Furthermore genes encoding proteins for G-protein coupled second messenger pathways such as adenylate cyclases, protein kinase A, cAMP responsive element binding proteins, phospholipase C and genes encoding for functions in gap junctions and genes encoding for ion channels and ion pumps could be expressed in the pharynx or in the neurons of the nematode.

The transgenic *C. elegans* described above can have a wild-type genetic background or can be mutant *C. elegans* strains. Preferably the worms are humanized, which means that a transgene which is a protein-encoding nucleic acid sequence of human origin is expressed in a worm made mutant for the *C. elegans* gene encoding the corresponding protein.

An extensive list of mutants which may be suitable for use in pharynx pumping assays can be found in *C. elegans* 11, CSHL press and in Neurobiology of the *C. elegans* Genome, C. I. Bargmann, Science 282:2028–2033. A complete list of G-proteins can be found in "The complete family of G-protein genes of *Caenorhabditis elegans*", Jansen G. to et al., the Worm Breeders Gazette, Vol. 15 (5), Feb. 1999.

Some examples of *C. elegans* mutants with mutations in genes encoding components of neuronal signalling pathways are listed below. The expression of transgenes encoding the corresponding *C. elegans* and human proteins can be engineered in *C. elegans* wild-type or *C. elegans* mutant strains resulting in transgenic and humanized worms respectively:

TABLE 1

| Neurotransmitters/pathway | *C. elegans* mutants |
| --- | --- |
| Acetylcholine | eat-18, eat-2, chat-1, unc-17 |
| Acetylcholine esterases | ace-i, ace-2, ace-3 |
| Nicotinic acetylcholine Receptors | unc-29, unc-38, lev-1, deg-3, acr-2 |
| Dopamine | cat-2, cat-4, bas-1, cat-1, cat-3, cat-5 |
| Serotonin | bas-1, mod-5, goa-1 |
| Glutamate | avr-15, eat-4, glr-1 |
| Acetylcholine | eat-18, eat-2, chat-1, unc-17 |
| Acetylcholine esterases | ace-i, ace-2, ace-3 |
| Nicotinic acetylcholine Receptors | unc-29, unc-38, lev-1, deg-3, acr-2 |
| GABA | unc-47, unc-25, unc-46, unc-49, exp-1 |
| Na+/K+ATPases subunits | eat-6 |
| Calcium channels | eat-12, unc-2, unc-36, unc-13 |
| Others | eat-5, unc-7, unc-18, rab-3, snt-1, ric-4, snb-1, unc-64, unc-50, unc-74 |

A range of *C. elegans* mutants may be obtained from the *C. elegans* mutant collection at the *C. elegans* Genetic Center, University of Minnesota, St Paul, Minnesota. Alternatively, specific mutants may be generated by standard methods. Such methods are described by Anderson in Methods in Cell Biology, Vol 48, "*C. elegans*: Modem biological analysis of an organism" Pages 31 to 58. Several selection rounds of the PCR technique can be performed to select a mutant worm with a deletion in a desired gene. Other methods of generating mutants with targeted defective gene expression are described by Sutton and Hodgkin, Zwaal et al and Fire et al as described above.

EXAMPLE 5

Dosage Response

To determine the sensitivity of the pharynx pumping assay, dilution series were made for some chemical substances. These include the chemicals clomipramine, tamoxifen, BP554, pimazide and thapsigargin. A concentration range was made from less than 1 $\mu$M up to 100 $\mu$M, and the pumping assay was repeated as described in previous examples. From these results distinct dose-response curves could be drafted.

This experiment shows clearly that the pharynx pumping assay is quantitative and can be used to determine the IC50 and ED50 of chemical substances.

Furthermore from this experiment the toxic effect of the chemical substance can be detected. The dosage response curve of the enhancer clomipramine shows clearly the toxic effect of the solvent DMSO at higher concentrations (FIG. 5).

Finally it is possible to detect the effect of a chemical substance on secondary targets or detect side effects of a chemical substance at various concentrations. This can be seen in the dosage response curve of thapsigargin, known to be an inhibitor of SERCA, which results in a decrease of the pumping rate of the *C. elegans* pharynx (FIG. 6). Nevertheless, at low concentration an enhancement of the pumping can be observed. This is the first observation of this feature of thapsigargin. Although further research is necessary to explain this behaviour, which could be caused by a still unknown secondary target of thapsigargin or another side effect, this experiment shows clearly the sensitivity of the pharynx assay, and the use of the pharynx assay to edit dosage response curves.

EXAMPLE 6

Detecting the Activity of Chemical Substances with Genetic Techniques

Other techniques exist to measure the pumping rate of the *C. elegans* pharynx. As the pharynx is muscle, the contractility of the pharynx is dependent on the internal calcium levels, These calcium levels can be measured using specific calcium-sensitive reporter genes.

It has been reported by Kerr et al. (West Coast Worm Meeting Abstract 77, 1998) that increased electrical activity can he detected indirectly by measuring the calcium levels in the *C. elegans* pharynx. The calcium sensitive reporter proteins described therein are Aequorin and GFP-calmodulin (Miyawaki et al., Nature 388:882–887).

In this study GFP-calmodulin was expressed in the pharynx of *C. elegans* and fluorescence was observed using two-photon microscopy. It has been shown that inhibitors of pumping such as ivermectin and enhancers of pumping such as serotonin influence the observed fluorescence of the GFP-calmodulin in a predicted way.

Analogous transgenic worms expressing GFP-calmodulin can be used to screen for chemical substances that influence the pumping rate of the nematode pharynx using the pharynx pumping assay methodology. Analogous to the pumping assay described for calcein-AM in the previous examples, the transgenic worms are placed in multi-well plates and chemical substances are added. The fluorescence of the GFP-calmodulin is then measured rather than calcein fluorescence using the same multi-well plate reader instrument.

With the use of appropriate promoter sequences, expression of aequorin or GFP-calmodulin can be engineered in other muscle tissues, or even in neurons in order to monitor the calcium levels in these cells. Such transgenics can be used in a screen as described above.

EXAMPLE 7

Genetic Enhancer and Suppressor Screens

Genes and hence biochemical pathways can be found that enhance, suppress or modulate the activity of a given compound. When applying a compound to the nematode *C. elegans*, phenotypic changes can be observed, however, the target of the compound or its mode of action can be known or be unknown. The screening method described below can be used to identify genes which suppress or enhance the activity of a compound which has a defined effect on the phenotype of *C. elegans*.

The compound 2,5-diphenyloxazole is an inhibitor of the pumping rate of the pharynx both in wild-type worms and in constitutive pumping worms. It is used herein as an example of a compound which has a defined effect on *C. elegans*.

*C. elegans* worms are subjected to random mutagenesis using standard techniques such as EMS, TMP-UV or radiation (Methods in Cell Biology, Vol. 48). The F1 generation of these mutagenized worms are placed worm by worm in the wells of multi-well plates and the worms allowed to grow and generate offspring. When the offspring have reached the desired growth stage, 2,5-diphenyloxazole and calcein-AM is added. The plates were further incubated for approximately one hour and fluorescence of the generated calcein was measured using a multi-well plate reader. Wells that had a higher fluorescence read-out were scored. The worms in these wells were used for further analysis, as they harbor a mutation in a gene or a pathway that suppresses the activity of 2,5-diphenyloxazole.

An analogous screen was performed with the compound doxepin, which is an enhancer of pharynx pumping. Mutants were scored that show a reduced pumping phenotype in the presence of the compound doxepin.

EXAMPLE 8

Screening for Antagonists of a Compound (Thapsigargin)

The compound thapsigargin is known to inhibit the activity of the sarco/endoplasmic reticulum calcium ATPase (SERCA). The SERCA protein pumps calcium into the sarco/endoplasmic reticulum and provides the cell with an internal storage of calcium. The internal storage of calcium is important for muscle activity. In *C. elegans*, inhibiting SERCA activity by applying thapsigargin to the worm results in a decrease in the pharynx pumping rate. Another feature observed by the action of thapsigargin on the nematode worm *C. elegans* is decreased movement, which is a result of the inhibition of SERCA activity of the body wall muscles.

A pharynx pumping screen has been developed to screen for chemical substances that suppress the activity of thapsigargin on SERCA. *C. elegans* nematodes, both wild-type nematodes and nematodes with a constitutive pumping pharynx are placed in the wells of multi-well plates as previous described. Thapsigargin is added to the worms at an inhibitory concentration and calcein-AM is added at a concentration of 5–10 $\mu$M as previous described. Finally chemical substances to be selected are added. Control wells are also set up containing thapsigargin alone with no second chemical substance.

Analogous to the pharynx pumping screen, fluorescence is measured using a multi-well plate reader. Wells harboring a chemical substance where the measured fluorescence is higher than in the control wells containing no chemical substance are scored. These wells harbor a chemical substance that is an antagonist of the thapsigargin activity, as the inhibitory activity of thapsigargin is suppressed. Chemical substances thus identified may inhibit directly the activity of thapsigargin, or stimulate the activity of SERCA, or have an enhancer activity on the SERCA pathway, and hence on the calcium biology of the organism.

Chemical substances selected in this screen are considered as potential therapeutics, or as hits for the further development of therapeutics in the disease areas which are the cause of a malfunction of the calcium biology of the organism. Examples of disease areas for which these therapeutics are useful are cardiac hypertrophy, cardiac failure, arterial hypertension, Type II diabetes and Brody disease.

In the example given above, thapsigargin is used as an example of a compound having a defined phenotypic effect on *C. elegans* and any compound that has an inhibitory activity on the pharynx pumping rate can be used in an analogous screen.

Screens to select for chemical substances that have an antagonist activity on compounds are known to enhance the pumping rate of the pharynx can also be performed. In such an experiment, a chemical substance is scored if it reduces the pumping rate of the pharynx in the presence of the compound known to be an enhancer of pharynx pumping.

Analogous experiments can be done with compound inhibiting other calcium pumps and even other ion pumps.

EXAMPLE 9

Screening for Chemical Substances in Transgenic, Mutant and Humanized Animals (SERCA-PLB)

The human SERCA-2 protein is known to be negatively regulated by at least one protein, known as phospholamban (PLB). Both are expressed in the heart of vertebrates, and an extensive list of literature exists on the features of this interaction.

An increase of the internal storage of calcium is general considered to be important for the strength of muscle contraction, and consequently an improvement or increase of this muscle contraction can be realized by enhancing the SERCA activity. Chemical substances that enhance the SERCA activity or inhibit the SERCA-PLB interaction are considered as potential therapeutics, or as hits for the further development of therapeutics in the disease areas which are the cause of a malfunction of the calcium biology of the cell or organism. Examples of disease areas where an increase of SERCA activity may be beneficial are cardiac hypertrophy, cardiac failure, arterial hypertension, Type II diabetes and Brody disease.

There are several SERCA genes and isoforms which are associated with different types of diseases; SERCA2 and PLB are associated with cardio-vascular diseases, SERCA1 and sarcolipin are associated with skeletal-muscle diseases, and three SERCA genes have been associated with non-insulin-dependent diabetes mellitus.

In order to perform screens to identify chemical substances which modulate the activity of SERCA pathways SERCA genes and PLB have been expressed in *C. elegans*. The expression of these genes can be regulated under the control of several specific promoters with the following activities:

a) The *C. elegans* myo-2 promoter which promotes expression in the pharynx b) The *C. elegans* SERCA promoter which promotes expression in the *C. elegans* muscles, including the pharynx, the vulva muscles and the body wall muscles. The following transgenics were constructed:

a) pig and/or human SERCA under the SERCA and/or myo-2 promoter.

b) pig and/or human SERCA under the SERCA and/or myo-2 promoter in a *C. elegans* mutated for the *C. elegans* SERCA (Knock-outs and selected mutants).

c) pig and/or human PLB under the SERCA and/or myo-2 promoter.

d) pig and/or human PLB under the SERCA and/or myo-2 promoter in a *C. elegans* mutated for the *C. elegans* SERCA (Knock-out and selected mutants).

e) pig and/or human PLB-GFP fusion under the SERCA and/or the myo-2 promoter.

f) pig and/or human PLB-GFP fusion under the SERCA and/or the myo-2 promoter in a *C. elegans* mutated for the *C. elegans* SERCA (Knock-outs and selected mutants).

g) pig and/or human SERCA under the SERCA promoter and pig and/or human PLB under the myo-2 promoter.

h) pig and/or human SERCA under the SERCA promoter and pig and/or human PLB under the myo-2 promoter in a *C. elegans* mutated for the *C. elegans*, SERCA (Knock-out and selected mutants).

i) pig and/or human SERCA under the SERCA promoter and pig and/or human PLB-GFP under the myo-2 promoter.

j) pig and/or human SERCA under the SERCA promoter and pig and/or human PLB-GFP under the myo-2 promoter in a *C. elegans* mutated for the *C. elegans* SERCA (Knock-out and selected mutants).

Some of these constructed transgenic and mutant animals show a clear change in pharynx pumping rate as could be measured by the fluorescence of calcein in the gut using the calcein-AM pharynx pumping assay. Some of these strains were considered to be useful for further screen development. As described in the previous examples, the transgenic and mutant animals were placed in the wells of multi-well plates. Calcein-AM and chemical substances under test were then added. The fluorescence of the calcein formed in the gut was measured in a multi-well plate reader set to measure fluorescence. Chemical substances that altered the properties of the pharynx pumping rate, and hence altered the function and activity of the SERCA pathway were selected for further analysis, and can be considered as potential compounds for therapeutic use, or as hits for the further development of therapeutics.

A analogous experiment can be performed with the SERCA1 gene and its regulator Sarcolipin (SLN), to detect chemical substances that alter their activity and/or regulation.

EXAMPLE 10

Screening for Chemical Substances in Transgenic and/or Mutant Animals (Neurodegeneration)

The anatomy of the pharynx of the nematode consists of several parts, containing several cells and cell types. These include the pharyngeal muscles, the pharyngeal epithelial cells, the pharyngeal glands, and the pharyngeal neurons. At least 14 neurons are involved in the function of the neuron from which the most important are 11, 12, 13, M3, MC, NSM, M1, RIP and M4 (reviewed in "The nematode *C. elegans* ed. by W. B. Wood, 1988, CSHL Press).

Mutations or dysfunctions in any part of the pharynx (the pharyngeal muscles, the pharyngeal epithelial cells, the pharyngeal glands, and the pharyngeal neurons) will result in an altered pumping rate of the pharynx. Several mutations are known in the literature to give rise to an altered pumping rate, or to have an altered pharynx morphology.

Another way to alter the cells involved in pharynx function, pharynx pumping and pharynx morphology is by applying using transgenic techniques to the nematode. Expression of toxic genes in one of the cells involved in pharynx anatomy and pharyngeal function will result in degeneration, dysfunction or abnormal development of the respectively cells. As a result the pumping rate of the pharynx will be altered, most probably the pumping rate will be decreased.

Examples of toxic genes that could be used to for this purpose are listed above. Transgenic *C. elegans* can be constructed which express these genes in a tissue specific way. For example, the myo-2 promoter will induce expression in the pharynx muscles, the unc-129 promoter will induce expression in the neuronal cells. For every cell type or tissue, a cell type-specific or tissue-specific promoter can be selected so that degeneration of the tissues can be precisely controlled. Promoters can be selected in such a way that the expression of the toxic gene is only induced in one specific cell. Mutants and transgenics that have an altered pharynx anatomy or pharynx pumping can then be used in a pharynx pumping screen to select for chemical substances that restore or rescue the genetic or morphological defect. If the mutant or transgenic animal has a decreased pumping rate the screen will preferentially identify chemical substances that enhance the pumping rate. If the mutant or transgenic shows an increased pumping rate, the screen will preferentially identify chemical substances that reduce the pumping rate of the pharynx

TABLE 2 examples of mutants which may be used in pharynx

| Gene | allele | Pharyngeal phenotype | Other phenotype |
| --- | --- | --- | --- |
| dig-1 | n1321 | Twisted | |
| eat-6 | ad467 | relaxation defective | ATPase |
| eat-13 | ad522 | relaxation defective | Slow growing |
| goa-1 | sy192 | increased pumping | hyperactive |
| mig-4 | rh51 | Twisted | |
| mlc-2 | | pumping defects | Larval lethal |
| pha-2 | ad427 | misshapen pharynx | Larval lethal |
| pha-3 | ad607 | misshapen pharynx | Slow growing |
| Phm-2 | ad538 | relaxation defective | |
| cha-1 | p1152 | slow pumping | Unc |
| clk-1 | e-2519 | slow pumping | Slow |
| eat-1 | ad427 | irregular pumping | Long and thin |
| eat-2 | ad451 | slow pumping | hypers. to cholin. agonist |
| eat-3 | | Very Slow pumping | Misformed |
| eat-4 | | pumping defects | |
| eat-5 | | unsynchronized pumping | |
| eat-7 | | sleeping | |
| eat-8 | | brief pumping | |
| eat-9 | | irregular pumping | slightly starved |
| eat-14 | | relaxation defects | motion defects |
| eat-18 | | slow pumping | starved |
| eat-x | | pumping defect | |
| Osm | | slow pumping | chemotaxis defects |
| snt-1 | | pumping defects | Unc |
| unc-11 | | slow pumping | Kinker |

TABLE 2-continued examples of mutants which may be used in pharynx

| Gene | allele | Pharyngeal phenotype | Other phenotype |
|---|---|---|---|
| unc-13 | | irregular pumping | Paralysed |
| unc-17 | | slow irregular pumping | Small |
| unc-26 | | slow pumping | little movement |
| unc-31 | | constitutive pumping | Slow |
| unc-36 | | irregular pumping | Paralysed |
| unc-57 | | slow pumping | Small |
| unc-58 | | sticky pumping | Shaker |
| unc-90 | | sticky pumping | Short |
| unc-105 | | sticky pumping | poor growth |
| sma-1 | | pharynx defects | |
| sma-2 | | reduced pumping | |
| sma-3 | | pharynx defects | |
| sma-4 | | pharynx defects | |
| exp-2 | sa26/+ | fast shallow pumping | jerky, egl, constipated |

EXAMPLE 12

Specific Example of the Assay with Dauers, Neurodegeneration and the Use of the Daf-7 Promoter The ASI neurons of *C. elegans* are chemical-sensory neurons and are essential for food perception and pharynx pumping. It has previously been reported that the disruption of the ASI or ADF or ASG or ASJ neuron results in dauer formation. These experiments that kill one or more of these neurons were performed with laser ablation. (Schackwitz WS et al., Neuron 17:719–728, 1996). Furthermore it was reported that the Daf-7 (a 10 member of the TGF-beta family) is expressed specifically in the ASI neuron.

In an experiment analogous to example 11, the ASI neuron has been killed, disrupted or altered in its properties. More specifically toxic genes have been expressed in this neuron by inducing their expression under the control of the daf-7 promoter. Disrupting the ASI neuron in such a way results in the formation of dauers.

Such strains were used in screens as previously described. In a first example the resulting dauers were used in a pharynx pumping assay. Dauer worms do not have or have only a reduced pharynx pumping. Chemical substances were identified that cause the worms to bypass the dauer phenotype and hence restore the pharynx pumping. As before, the rate of pharynx pumping was measured using calcein-AM.

In a second example the dauers were submitted to the movement assay. As dauer worms do not move, and hence precipitate in the wells, they can be used in the movement assay to identify chemical substances that cause the worms to bypass the dauer phenotype and hence alter the movement of the worms. The movement behaviour of the worms was detected using autofluorescence over the center of the wells.

EXAMPLE 13

Specific Example of the Assay, with dauers

Daf-2 ts is a nematode mutant, which grows normally at 15° C. but generated 100% dauer formation at 25° C., these mutants can also be used in screens to isolate chemical substances that cause worms to bypass the dauer phenotype.

To perform such an assay synchronized L1 Daf-2 ts worms are distributed over the wells of microtiter plates. Synchronized eggs could also have been used. The worms were supplied with food and grown further at 25° C., resulting in dauer formation. After approximately 4 days the chemical under test and calcein-AM is added and fluorescence is measured at selected time intervals, varying from 1 hour to 4 days, keeping the temperature at 25° C. Chemical compounds were scored that caused the worms to bypass the dauer phenotype. Due to the presence of the food substrate, it may be difficult to detect fluorescence using a multi-well plate reader. The FANS device may alternatively be used to measure fluorescence in this instance.

An analogous experiment can be performed in which the chemical under test is added to the wells, approximately together with the L1 worms.

In another variant of this experiment, large quantities of Daf-2 ts dauers were cultivated. The dauers were then dispensed over the wells of multi-well plates and chemical substances were added. The multi-well plates were placed in a multi-well plate reader set up to perform a movement assay (i.e. to measure autofluorescence).

Autofluorescence measurements were recorded at several time intervals varying from 1 hour to 4 days, keeping the wells at 25° C.

EXAMPLE 14

Screening for Chemical Substances and Compound Antagonists with the Movement Assay The nematode mutant (ace-1; ace-2) does not show any movement and has a spasm-like phenotype. The worm does not show any sinusoidal shape, but is straight shaped.

This is because the mutant is mutated in the acetylcholine esterases, resulting in high concentrations of acetylcholine in the synapses. Neostigmine, a well known acetylcholine esterase inhibitor, was added to wild-type worms distributed over the wells of a multi-well plate and submitted to the movement assay after approximately 2 hours. As FIG. 8, panel 1 shows clearly worms exposed to neostigmine showed a clear decrease in movement.

Hexamethonium and mecamylamine are well known acetylcholine receptor antagonists and hence should repress the overload of acetylcholine in the synapses of the ace1; ace2 mutant, resulting in restoration or rescue of the movement. As receptor antagonist, hexamethonium will also result in a decrease of movement, as it prevents proper signalling. In last panel of FIG. 8, it is clearly shown that hexamethonium represses the movement of wild-type worms, but significant less than neostigmine (100% represents normal movement of wild-type worms).

In another experiment, wild-type worms were contacted with inhibitory concentrations of neostigmine to prevent movement. After a small incubation period, various concentrations of hexamethonium were added and the wells were submitted to the movement assay (measurement of autofluorescence). As FIG. 8 shows, increasing concentrations of hexamethonium resulted in more movement as predicted (hexamethonium is an antagonist), but the upper limit seems to be determined by the inhibitory activity of hexamethonium. At very high concentrations of hexamethonium (although lower than the concentrations shown in last panel) a toxic effect is observed, resulting in a decrease in movement. This toxic effect is probably due to the presence of high concentrations of both neostigmine and hexamethonium.

An analogous experiment was performed with the ace-1; ace-2 double mutant. In this experiment, increasing concentrations of hexamethonium were added to the wells in the absence of neostigmine. The results of both experiments were comparable.

This experiment shows clearly the applicability of the movement assay to select for chemical substances and antagonists of selected compounds.

EXAMPLE 15

Example of a Mating Assay Using Hermaphrodite Non-selfers

High throughput analysis of the nematode mating behaviour could be performed by counting the offspring of the mating experiment. First, equal amounts of male worms were distributed over the wells of multi-well plates. Hermaphrodites were then added over the wells in such a way that every well contains an equal amount of hermaphrodites. The ratio between males and hermaphrodites can be varied from experiment to experiment. The hermaphrodite chosen in this experiment has a reduced self-offspring or the offspring is non-viable or preferentially the hermaphrodite is self-sterile, such as the hermaphrodites mutant in the fer or spe genes. Furthermore, to enhance mating the self-sterile hermaphrodite has preferentially a reduced movement or no movement phenotype. The males in this experiments can be wild-type males, or mutant males, or transgenic males, or humanized males.

Mating behaviour is assessed by measuring the total number of offspring produced, as described above.

EXAMPLE 16

Example of a Mating Assay Hermaphrodite Non-selfers Expressing GFP

A mating assay has also been performed with a specific self-sterile transgenic hermaphrodite that has a reduced movement phenotype and expresses stably GFP. All offspring of this mating assay express GFP and hence the number of offspring can easily be detected by measuring the GFP fluorescence using a multi-well plate reader or a FANS. Hermaphrodites expressing other markers such as luminescent markers can be used in an analogous experiment.

EXAMPLE 17

Example of a Mating Assay Males Expressing GFP

In another variant of the mating assay the hermaphrodites were chosen in the following combinations:
a) The hermaphrodites were wild-type hermaphrodites, or hermaphrodites showing a reduced movement phenotype
b) The male nematodes were wild-type, transgenic, mutant or humanized nematodes, expressing GFP.

In this experiment, the offspring of the self-fertilization of the hermaphrodite, and the offspring resulting from the genuine mating could be distinguished by following the fluorescence of the GFP as only the offspring resulting from a mating showed GFP expression.

EXAMPLE 18

Male-specific Neurons

The following Table 3 lists C. elegans male-specific neurons and their role in mating behaviour. Disruption of one or more of these neurons, for example by expression of a toxic gene, may result in C. elegans variants which can be useful in mating screens.

TABLE 3

| Neuron | Structure | Class | Role |
|---|---|---|---|
| Can | ventral cord | motor | ? |
| CPn | ventral cord | motor | turning |
| CEMn | head | sensory | ? |
| DXn | | motor | ? |
| DVE | | inter | ? sperm activation or transfer |
| DVF | | inter | ? sperm activation or transfer |
| Efn | | | turning |
| HOA | hook | sensory | vulva location |
| HOB | hook | sensory | vulva location |
| PCA | p.c.s. | sensory | vulva location |
| PCB | p.c.s. | sensory | vulva location |
| PCC | p.c.s. | sensory | vulva location |
| PGA | p.a.g. | inter | ? |
| PGA | p.a.g. | inter | ? |
| PVV | p.a.g. | inter | ? |
| PVY | p.a.g. | inter | backing |
| R1A | ray | sensory | dorsal response? |
| R1B | ray | sensory | dorsal response? |
| R2A | ray | sensory | ventral response? |
| R2B | ray | sensory | ventral response? |
| R3A | ray | sensory | ? |
| R3B | ray | sensory | ? |
| R4A | ray | sensory | ventral response? |
| R4B | ray | sensory | ventral response? |
| R5A | ray | sensory | dorsal response? turning? |
| R5B | ray | sensory | dorsal response? |
| R6A | ray | sensory | ? |
| R6B | ray | sensory | ? |
| R7A | ray | sensory | dorsal response? |
| R7B | ray | sensory | dorsal response? turning? |
| R8A | ray | sensory | ventral response? turnimg? |
| R8B | ray | sensory | ventral response? turning? |
| R9A | ray | sensory | turning? |
| R9B | ray | sensory | turning? |
| SPC | spicule | motor/proprio | spicule insertion |
| SPD | spicule | sensory | spicule insertion |
| SPV | spicule | sensory | inhibits ejaculation |

EXAMPLE 19

Further Mutant and Transgenic C. elegans

The following Table 4 lists C. elegans mutants which show abnormalities in male mating behaviour which may be used in the mating assays:

TABLE 4

| Gene (Mutant) | Defect |
|---|---|
| cat-1, cat-2, cat-4, cod-5 | Turning |
| che-2, che-3, che-4, cod-10 | Response to contact |
| cod-1, cod-2, cod-4, cod-6, cod-7, cod-8 | Spicule insertion |
| cod-12, cod-13, cod-14, cod-15 | Vulva location |
| ram-1, ram-2, ram-3, ram-4, ram-5 | Ray morphology |

The following Table 5 lists mutant C. elegans which may be used in the egg laying assays:

TABLE 5

| Gene (Mutant) | Defect |
|---|---|
| egl-1, egl-43 | HSN function migration and differentiation |
| egl-1, sem-1, sem-4 | vulva muscle development |
| egl-15, egl-17 | sex myoblast migration |
| egl-10, egl-30 | synaptic transmission |

The egg laying assay can also be performed using transgenic C. elegans which exhibit altered egg laying behaviour as a result of the expression of a toxic gene in a specific tissue or cell type. Suitable transgenic *C. elegans* can be constructed according standard techniques known in the art using one of the toxic genes listed above under the control of an appropriate tissue- or cell type-specific promoter. Promoters which may be useful for this purpose include the lin-31, egl-17, unc-17 and unc-53 promoters. The following Table 6 lists mutant *C. elegans* which may be used in the defecation assays:

TABLE 6

| Gene (Mutant) | Defect |
|---|---|
| aex-1; aex-2, aex-3, aex-4; aex-5, aex-6 | aBoc and expulsion |
| unc-25; unc-47; exp-1; exp-2 | constipated (expulsion) |
| pho-1 to pho-7, egl-8 | aBoc specific |
| dec-l, dec-2, dec-4, dec-7, dec-11, dec-12 | defecation cycle |

The defecation assays can also be performed using transgenic *C. elegans* which exhibit altered defecation behaviour as a result of the expression of a toxic gene in a specific tissue or cell type. Suitable transgenic *C. elegans* can be constructed according standard techniques known in the art using one of the toxic genes listed above under the control of an appropriate tissue- or cell type-specific promoter. Promoters which may be useful for this purpose include the unc-43 and unc-25 promoters.

The following Table 7 lists mutant *C. elegans* which may be used in the movement assays:

TABLE 7

| Gene (Mutant) | Defect |
|---|---|
| unc-17 | acetylcholine receptor; coiler |
| ace-1; ace-2 | acetylcholine esterase; loopy head movement |
| unc-25; unc-47 | GABA; shrinker |
| unc-15; unc-54 | paramyosin, myosin; paralysed |
| unc-36 | Ca channel; paralysed |

TABLE 8

Enhancers of the *C. elegans* pharynx pumping rate isolated from the pharmacopoeia.

| Compound name | Mode of Action | Disease area | Positives after 1 hour incubation |
|---|---|---|---|
| Clomipramine | ser uptake inhibitor | Antidepressant | |
| Amitriptyline | ser uptake inhibitor | Antidepressant | |
| Desipramine | ser uptake inhibitor | Antidepressant | |
| Fluvoxamine | ser uptake inhibitor | Antidepressant | |
| Nortriptyline | ser uptake inhibitor | Antidepressant | |
| Imipramine | ser uptake inhibitor | Antidepressant | |
| Fluoxetine | ser uptake inhibitor | Antidepressant | + |

TABLE 8-continued

Enhancers of the *C. elegans* pharynx pumping rate isolated from the pharmacopoeia.

| Compound name | Mode of Action | Disease area | Positives after 1 hour incubation |
|---|---|---|---|
| Doxepin | unknown | Antidepressant, Antipruritic | + |
| Nordoxepin | unknown | Antidepressant, Antipruritic | + |
| Mianserin | 5HT antagonist | | + |
| Norclomipramine | ser uptake inhibitor | Antidepressant | |
| Cyproheptadine | ser receptor antagonist | Antihistaminic; antipruritic; appetite stim. | |
| Cyclobenzaprine | * | Psychomotor depressant; muscle relaxant | |

TABLE 9

Inhibitors of the *C. elegans* pharyrix pumping rate isolated from the pharmacopoeia.

| Compound name | Mode of Action | Disease area | Positives after 1 hour incubation |
|---|---|---|---|
| Pimozide | D2 antagonist | Antipsychotic | |
| Haloperidol | D2 antagonist | Alzheimer, Antipsychotic | |
| Trazadone | serotonin uptake blocker metabolite D2 antagonist 5HT1-agonist | Alzheimer, Antidepressant Antipsychotic | |
| BP554 | 5HT1-agonist | | |
| Ivermectin | chloride channel blocker | Antihelmintic | |
| Levamisole | | Antihelmintic | |
| Metrifonate | cholinesterase inhibitor | Antihelmintic, Alzheimer | + |
| Physostigmine | cholinesterase inhibitor | Alzheimer | + |
| Tamoxifen | chloride channel blocker | Antihistamine | |
| Flunarizine | Na/Ca channel blocker | Antipsychotic | |
| Thapsigargin | "calcium channel blocker" | | |
| alpha NETA | choline acetyl transferase inhibitor | | |
| Atropine | cholinergic antagonist | | + |
| L-Hyoscyamine | cholinergic antagonist | Active form of atropine | + |
| Diphenyl-hydantoin | | Anticonvulsant, antiepileptic | + |
| ZAPA | GABA-antagonist | | + |
| 2,5-diphenyloxazole | | | |

TABLE 10 partial list of hits obtained when screening 800 compounds from a pharmacopoeia library using a movement assay with *C. elegans*. The hit compounds were scored as causing a detectable change in the movement behaviour of *C. elegans*.

| | | | | | | | |
|---|---|---|---|---|---|---|---|
| Harmane HCl | 9 | B4 | 1843115 | 555251 | 6085,208 | 1773,442 | — |
| TPMPA | 8 | H6 | 21792 | 120778 | 71,94823 | 385,7584 | HIT |
| Prazosin | 4 | E9 | 94689 | 113608 | 312,6242 | 362,8578 | HIT |
| Vigabatrin | 6 | H7 | 20828 | 61410 | 68,7655 | 196,1402 | HIT |
| (2S,3R)-Chloropheg MSOPPE | 6 | H8 | 21514 | 48736 | 71,03039 | 155,6601 | HIT |
| MSOPPE | 6 | E7 | 23760 | 44614 | 78,44576 | 142,4947 | HIT |
| (n)-Acetylcarnitine | 2 | C10 | 23457 | 44156 | 77,44537 | 141,0319 | HIT |
| DPPE | 5 | G11 | 20365 | 43629 | 67,23686 | 139,3487 | HIT |
| Indole-2-carboxylic acid | 2 | A4 | 19362 | 43403 | 63,92537 | 138,6268 | HIT |
| N-desisopropyl propanolol | 6 | A7 | 23737 | 43102 | 78,36982 | 137,6654 | HIT |
| YS-035 | 3 | E3 | 21415 | 42457 | 70,70353 | 135,6054 | HIT |
| L-AP5 | 1 | G2 | 21446 | 42393 | 70,80588 | 135,4009 | HIT |
| 2,4-Dihydroxy phenyl acetyl-L-asparagine | 2 | G4 | 18057 | 42203 | 59,61679 | 134,7941 | HIT |
| L-AP3 | 2 | G2 | 22073 | 41858 | 72,87597 | 133,6922 | HIT |
| D-AP5 | 1 | F2 | 19717 | 41697 | 65,09743 | 133,178 | HIT |
| O-Phospho-L-serine | 1 | A3 | 20292 | 41086 | 66,99584 | 131,2265 | HIT |
| Clofibric acid | 6 | D9 | 22933 | 40916 | 75,71534 | 130,6835 | HIT |
| cis-Azetidine-2,4-dicarboxylic acid | 7 | D8 | 19503 | 40568 | 64,39089 | 129,572 | HIT |
| L-AP4 | 1 | C2 | 19824 | 39523 | 65,4507 | 126,2343 | HIT |
| Spaglumic acid | 3 | E6 | 20295 | 38417 | 67,00575 | 122,7018 | HIT |
| Arecaidine but-2-ynyl ester | 2 | F5 | 20002 | 37675 | 66,03838 | 120,3319 | HIT |
| Cycloleucine | 2 | E4 | 19234 | 36560 | 63,50276 | 116,7707 | HIT |
| S(-)-Atenolol | 3 | G6 | 18176 | 36336 | 60,00968 | 116,0552 | HIT |
| Propanolol glycol | 6 | D7 | 17134 | 34849 | 56,56943 | 111,3058 | H1T |
| GF 109203X | 5 | E11 | 15685 | 34448 | 51,78542 | 110,025 | HIT |
| Ketoconazole | 8 | G11 | 15803 | 33531 | 52,17501 | 107,0962 | HIT |
| DL-2-Aminosuberic acid | 1 | H2 | 17141 | 33518 | 56,59254 | 107,0547 | HIT |
| HU 210 | 7 | B9 | 15481 | 33514 | 51,1119 | 107,0419 | HIT |
| GR 46611 | 7 | F8 | 15815 | 33199 | 52,21463 | 106,0358 | HIT |
| 7-(Dimethyl carbamoyloxy)-6-phenylpyrrolo | 6 | C2 | 14278 | 32900 | 47,14009 | 105,0808 | HIT |
| GBLD 345 | 6 | G3 | 12620 | 32858 | 41,66605 | 104,9467 | HIT |
| L-701,324 | 7 | E6 | 14647 | 32476 | 48,35837 | 103,7266 | HIT |
| tADA | 7 | E8 | 16096 | 32342 | 53,14238 | 103,2986 | HIT |
| RS 17053 | 8 | B10 | 14439 | 32050 | 47,67164 | 102,366 | HIT |
| N-Benzyl naltrindole | 6 | G6 | 14932 | 31760 | 49,29933 | 101,4397 | HIT |

TABLE 11

Enhancers of *C. elegans* pharynx pumping found from screening the Tocris compound library (Bristol, UK) using a pharynx pumping assay.

| Name | Known pharmacological activity |
|---|---|
| Clomipramine | serotonin uptake inhibitor |
| 6-Nitroquipazine | serotonin uptake inhibitor |
| Fluvoxamine | Serotonin uptake imhibitor |
| Methiothepin | 5HT1,2 antagonist |
| 5-Nonyloxytryptamine oxalate | 5HT1B antagonist |
| N-Desmethylclozapine | 5HT2C antagonist |
| 3-Methoxycarbonylamino-b-carboline | benzodiazepine receptor inhibitor |
| 7-(Dimethylcarbamoyloxy)-6-phenylpyrrolo | benzodiazepine receptor inhibitor |
| Nimodipine | Ca channel blocker |
| CP 55,940 | cannabinoid agonist |
| WIN 55,212-2 | cannabinoid agonist |
| WIN 64338 | cannabinoid agonist |
| HU 210 | cannabinoid agonist |
| Bromocriptine | D2 agonist |
| 1-(2-Benzo[b]thienyl)-N-butylcyclohexanamine | dopamine uptake inhibitor |
| 1-[1-(2-Benzo[b]thienyl)-cyclohexyl]pyrrolidine | dopamine uptake inhibitor |
| 2-amino-4-methylpyridine | iNOS inhibitor |
| 17-ODYA | leukotryiene B4 hydrolase inhibitor |
| Etazolate | PDE4 inhibitor |
| Cis-(n)-N-methyl-N-[2-(3,4-dichlorophenyl)- | sigma receptor ligand |
| N-exo-Bicyclo[2,2,1]hept-2-yl-N'-(2-iodophenyl)- | sigma receptor ligand (haloperidol sensitive) |
| L-732,138 | substance P receptor antagonist |
| Cyclosporin A | calcineurin phosphatase activity inhibitor |

TABLE 11-continued

Enhancers of *C. elegans* pharynx pumping found from screening the Tocris compound library (Bristol, UK) using a pharynx pumping assay.

| Name | Known pharmacological activity |
|---|---|
| Dioctanoylglycol | diacyl glycerol kinase inhibitor |
| LY 225910 | CCKB receptor antagonist |
| a-NETA | choline acetyl transferase inhibitor |
| 4-Naphthalimidobutyric acid | aldose reductase inhibitor |
| Ergotamine | antimigraine oxytocic |

All references disclosed herein are incorporated by reference in their entirety

We claim:

1. A method of identifying chemical substances which have potential pharmacological activity using nematode worms, which method comprises the steps of:
   (a) dispensing substantially equal numbers of nematode worms into each of the wells of a multi-well assay plate;
   (b) contacting the nematode worms with a chemical substance;
   (c) detecting a signal indicating phenotypic, physiological, behavioral, or biochemical changes in the nematode worms using non-visual detection means;
   wherein step (a) is performed in a multi-well plate with liquid assay medium containing a water soluble polymer at a concentration sufficient to increase the viscosity of the medium;
   wherein the water soluble polymer is medium viscosity carboxymethyl cellulose.

2. A method of identifying chemical substances which have potential pharmacological activity using nematode worms, which method comprises the steps of:
   (a) dispensing substantially equal numbers of nematode worms into each of the wells of a multi-well assay plate;
   (b) contacting the nematode worms with a chemical substance;
   (c) detecting a signal indicating phenotypic, physiological, behavioral, or biochemical changes in the nematode worms using non-visual detection means;
   wherein step (a) is performed in a multi-well plate with liquid assay medium containing a water soluble polymer at a concentration sufficient to prevent the nematode worms from sticking to the wells of the multi-well plate.

3. The method as claimed in claim 2 wherein the water soluble polymer is polyethylene glycol, polyvinyl alcohol, or polyvinylpyrrolidone.

4. A method of identifying chemical substances which have potential pharmacological activity using nematode worms, which method comprises the steps of:
   (a) dispensing substantially equal numbers of nematode worms into each of the wells of a multi-well assay plate;
   (b) contacting the nematode worms with a chemical substance;
   (c) detecting a signal indicating phenotypic, physiological, behavioural, or biochemical changes in the nematode worms using non-visual detection means,
   wherein the assay is carried out in a liquid medium having a viscosity greater than M9 medium.

5. The method as claimed in claim 4 wherein the nematode worms are microscopic nematodes.

6. The method as claimed in claim 5 wherein the nematode worms are *C. elegans* or *C. briggsae*.

7. The method as claimed in claim 4 wherein the step of detecting a signal comprises detecting a change in a measurable property of a marker molecule, whereby a change in the property of the marker molecule indicates a phenotypic, physiological, behavioural, or biochemical change in the nematode worms.

8. The method as claimed in claim 7 wherein the marker molecule is a fluorescent molecule, a luminescent molecule, or a coloured molecule.

9. The method as claimed in claim 7 wherein the marker molecule is a precursor of a fluorescent molecule, a precursor of a luminescent molecule, or a precursor of a coloured molecule.

10. The method as claimed in claim 9 wherein said marker molecule is capable of being cleaved by the action of an enzyme present in the gut of *C. elegans* to generate a fluorescent molecule, a luminescent molecule, or a coloured molecule.

11. The method as claimed in claim 4 wherein the non-visual detection means is a multi-well plate reader.

12. The method as claimed in claim 11 wherein the multi-well plate reader performs luminescence, fluorescence, or spectrophotometric detection.

13. The method as claimed in claim 4 wherein the non-visual detection means is a fluorescence activated nematode screening and sorting (FANS) device.

14. The method as claimed in claim 13 wherein the FANS device performs luminescence, fluorescence, or spectrophotometric detection.

15. The method as claimed in claim 4 wherein step (a) comprises dispensing substantially equal volumes of a homogeneous suspension of nematode worms into each of the wells of the multi-well assay plate.

16. The method as claimed in claim 15 wherein the homogeneous suspension comprises a suspension of *C. elegans* in a viscous solution.

17. The method as claimed in claim 16 wherein the viscous solution comprises a solution of a polymer material.

18. The method as claimed in claim 17 wherein the polymer material is low melting point agarose.

19. The method as claimed in claim 4 wherein the nematode worms are synchronized in the same growth stage.

20. The method as claimed in claim 19 wherein the nematode worms are eggs, L1 stage, L2 stage, L3 stage, L4 stage, adult worms, or dauer worms.

21. The method as claimed in claim 19 wherein the worms are hermaphrodites or males.

22. The method as claimed in claim 4 wherein the nematode worms are a wild type strain, a mutant strain, a transgenic strain, or a humanized strain.

23. The method as claimed in claim 4 wherein step (a) is performed in a multi-well plate with liquid assay medium containing a water soluble polymer at a concentration sufficient to increase the viscosity of the medium.

24. The method as claimed in claim 23 wherein the water soluble polymer is carboxymethyl cellulose, low melting point agarose, or polyethylene glycol.

25. The method as claimed in claim 24 wherein the water soluble polymer is medium viscosity carboxymethyl cellulose.

26. The method as claimed in claim 4 wherein step (a) is performed in a multi-well plate with liquid assay medium containing a water soluble polymer at a concentration sufficient to prevent the nematode worms from sticking to the wells of the multi-well plate.

27. The method as claimed in claim 26 wherein the water soluble polymer is polyethylene glycol, polyvinyl alcohol, or polyvinylpyrrolidone.

* * * * *